(12) United States Patent
Duan et al.

(10) Patent No.: US 8,802,702 B2
(45) Date of Patent: Aug. 12, 2014

(54) COMPOUNDS FOR REDUCING DRUG RESISTANCE AND USES THEREOF

(75) Inventors: Zhenfeng Duan, Cambridge, MA (US); Francis J. Hornicek, Burlington, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/144,228

(22) PCT Filed: Jan. 15, 2010

(86) PCT No.: PCT/US2010/021158
§ 371 (c)(1),
(2), (4) Date: Sep. 28, 2011

(87) PCT Pub. No.: WO2010/083385
PCT Pub. Date: Jul. 22, 2010

(65) Prior Publication Data
US 2012/0035126 A1    Feb. 9, 2012

Related U.S. Application Data

(60) Provisional application No. 61/205,251, filed on Jan. 15, 2009.

(51) Int. Cl.
*A61K 31/47* (2006.01)

(52) U.S. Cl.
USPC .......................................................... 514/314

(58) Field of Classification Search
USPC .......................................................... 514/314
See application file for complete search history.

(56) References Cited

FOREIGN PATENT DOCUMENTS

WO    WO 2008027912 A2 *  3/2008

OTHER PUBLICATIONS

Ivnitski-Steele, I. et al. ASSAY and Drug Development Technologies vol. 6, pp. 263-276. Published 2008.*
Huncharek, M. et al. Melanoma Research vol. 11, pp. 75-81. Published 2001.*
Stedman's Medical Dictionary 27th Edition, pp. 865-866 Published 2000.*
Cecil's Textbook of Medicine. 21st Edition. pp. 1060-1074. Published 2000.*
Duan, Z., et al. J. Med. Chem. vol. 55, pp. 3113-3121. Published 2012.*
Rothe, W.E., et al., J. Med. Chem. vol. 11, pp. 366-368. Published 1968.*
Solary, E. et al., Blood., vol. 88, pp. 1198-1205. Published 1996.*
Herweijer, H., et al. Br. J. Cancer, vol. 63, pp. 663-669. Published 1991.*
Stan B. Kaye et al., "Reversal of Drug Resistance in Ovarian Cancer: Where Do We Go From Here?," Journal of Clinical Oncology 2008 26:2616-2618.
Gergely Szakacs et al., "Targeting multidrug resistance in cancer," Nature Reviews Drug Discovery 2006 5:219-234.
Rothe and Jacobus, "Laboratory Evaluation of gthe Phototoxic Potency of Quinolinemethanols," Journal of Medicinal Chemistry 1968 11:366-368.
AnaSpec, "DHL™ Cell Cytotoxicity Assay Kit," Catalog #71302, Version 2.1, Sep. 17, 2007, 5 pages.
ScienCell Research Laboratories, "LDH Cytotoxicity Assay," Cat. No. 8078, Aug. 4, 2010, 3 pages.
Sigma, "In Vitro Toxicology Assay Kit MTT Based," Stock No. TOX-1, Jul. 25, 2007, 2 pages.
Sigma, "In Vitro Toxicology Assay Kit Neutral Red Based," Stock No. TOX-4, Apr. 30, 2004, 2 pages.
AnaSpec, "DHL™ Cell Cytotoxicity Assay Kit," Catalog #71302, Version 2.1, Sep. 17, 2007.
Chemicon International, "Multidrug Resistance Direct Dye Efflux Assay," Cat. No. ECM910 (2003).
Le and Bast, "Src family kinases and paclitaxel sensitivity," Cancer Biology & Therapy, 12(4):260-269 (2011).
Lippert et al., "Current Status of Methods to Assess Cancer Drug Resistance," Int. J. Med. Sci., 8:245-253 (2011).
Nooter and Herweijer, "Multidrug resistance (*mdr*) genes in human cancer," Br. J. Cancer, 63:663-669 (1991).
ScienCell Research Laboratories, "LDH Cytotoxicity Assay," Cat. No. 8078, Aug. 4, 2010.
Sigma, "In Vitro Toxicology Assay Kit MTT Based," Stock No. TOX-1, Jul. 25, 2007.
Sigma, "In Vitro Toxicology Assay Kit Neutral Red Based," Stock No. TOX-4, Apr. 30, 2004.
Tidefelt et al, "P-Glycoprotein inhibitor Valspodar (PSC 833) Increases the Intracellular Concentrations of Daunorubicin In Vivo in Patients With P-Glycoprotein—Positive Acute Myeloid Leukemia," J. Clin. Oncol., 18:1837-1844 (2000).

* cited by examiner

*Primary Examiner* — Paul Zarek
*Assistant Examiner* — George W Kosturko
(74) *Attorney, Agent, or Firm* — Fish & Richardson P.C.

(57) ABSTRACT

This invention provides compounds capable of reducing drug resistance in a subject undergoing cancer treatment, methods using the compounds, compositions, and methods for identifying such compounds.

23 Claims, 10 Drawing Sheets

Effect of small molecule NSC77037 ("B") and NSC23925 ("A") on drug sensitivity in osteosarcoma drug resistant cells

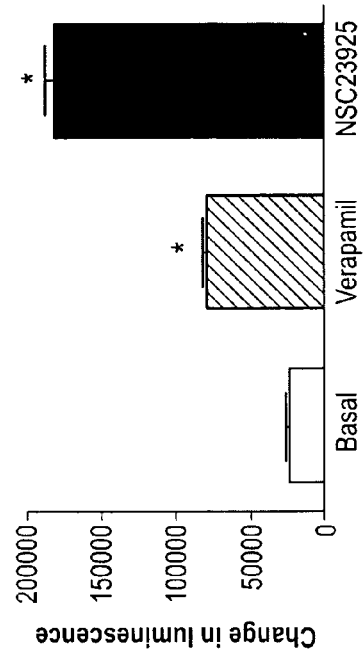
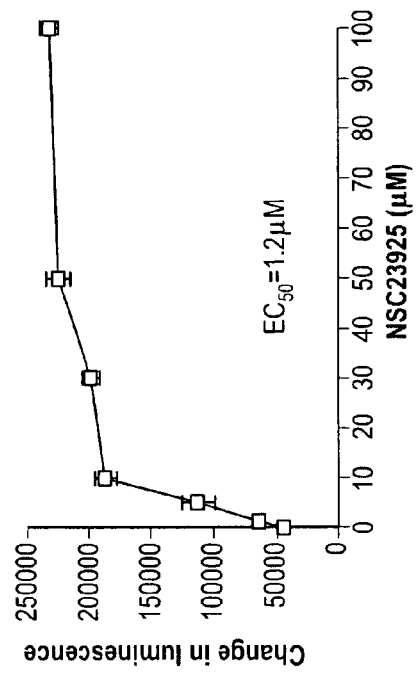
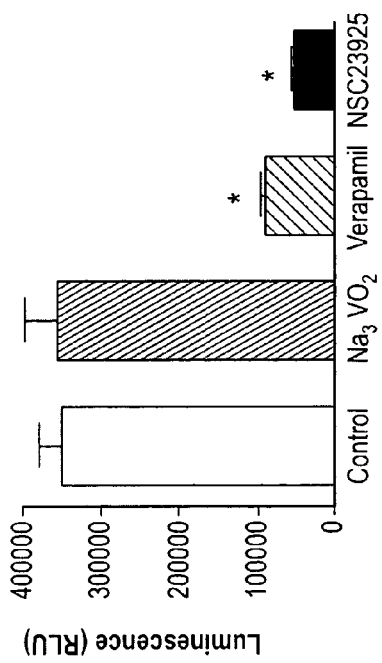
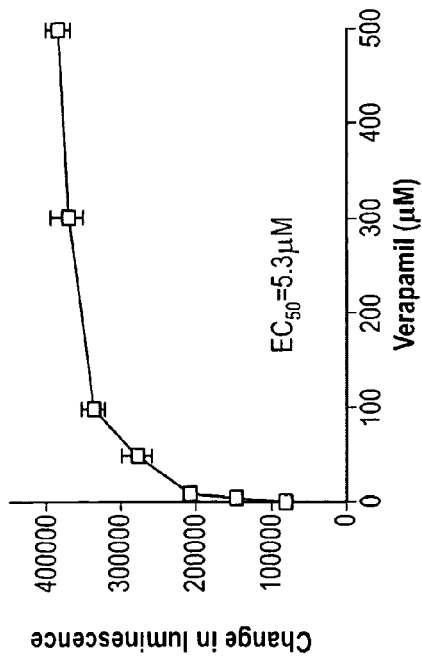
FIG. 6A
FIG. 6B
FIG. 6C
FIG. 6D

COMPOUNDS FOR REDUCING DRUG RESISTANCE AND USES THEREOF

RELATED APPLICATIONS

This application is a 371 application of International Application No. PCT/US2010/021158, filed on Jan. 15, 2010, and claims priority to U.S. provisional application Ser. No. 61/205,251, filed Jan. 15, 2009, the entire contents of which are hereby incorporated by reference.

BACKGROUND OF THE INVENTION

Cancer is a serious health issue all around the world. Cancer affects people at all ages, even fetuses. As reported by the World Health Organization in 2007, cancer causes about 13% of all deaths. About 7.6 million people died from cancer in the world during 2007.

Cancer is a disease resulting from an abnormal growth of tissue. Certain cancers have the potential to invade into local tissues and also metastasize to distant organs. The disease can develop in a wide variety of different organs, tissues and cell types. Therefore, the term "cancer" refers to a collection of over a thousand different diseases.

Despite recent advancements made in treating cancers, it is often observed that with very few exceptions, a cancer treatment fails to cure a patient. One of the main causes of failure in the treatment of cancer is the development of drug resistance by the cancer cells. In other words, after several cycles of chemotherapy, some tumor cells become resistant to the chemotherapeutic agent, which results in a loss of response to further therapy. This is a very serious problem that may lead to recurrence of disease or even death.

In these cases, tumors can be resistant to a variety of anti-cancer drugs with different structures and mechanism of action. Mechanisms of resistance extrinsic to cancer cells include altered pharmacokinetics, poor drug penetration through the extracellular matrix, cell adhesion and increased intratumoral hydrostatic pressure. Intrinsic cellular resistance further decreases the effectiveness of chemotherapy. Although there are several different intrinsic cellular mechanisms associated with the development of drug resistance, a common cause is believed to be overexpression of a plasma membrane glycoprotein (Pgp).

Pgp is the best known and most important mediator of drug resistance. This gene product belongs to the ABC (ATP binding cassette) superfamily of transporter proteins, and it acts as an energy-dependent drug efflux pump, preventing adequate intracellular accumulation of a broad range of cytotoxic drugs for cell kill. Pgp expression, frequently detected in the solid, hematologic cancers found in humans, as well as recently reported cancer stem cells, is a marker of chemoresistance or decreased survival in leukemia, lymphoma, osteosarcoma, small-cell lung cancer, ovarian cancer, breast cancer, and many other malignancies. Innate or acquired expression of Pgp, therefore, is a major problem in cancer chemotherapy.

Numerous efforts have been made in the art to overcome drug resistance. A broad range of compounds that interact with Pgp and block drug efflux have been reported to reverse the drug resistance phenotype. Unfortunately, it has been reported that the majority of these chemosensitizers lack in vivo activity due to problems associated with maintaining active doses without causing serious side effects. For instance, for verapamil, a calcium channel blocker, the doses required to modify drug resistance are associated with cardiac toxicity. Another example is CsA, which has been found to exert immunosuppressive effects and nephrotoxicity. Also, it was reported that PSC 833 causes cerebellar ataxia and hyperbilirubinemia toxicities. In addition, many of these Pgp inhibitors are compounds developed for other clinical uses and therefore lacked sufficient potency and/or specificity. Many of these Pgp inhibitors exhibit non-target-related toxicities that compromise the achievement of therapeutic exposures.

Therefore, there is an unmet clinical need for development of potent and selective drug resistance inhibitors to reduce the severity or incidence of the drug resistance in a cancer chemotherapy.

SUMMARY OF THE INVENTION

One aspect of the invention provides a method of reducing drug resistance in a subject undergoing cancer treatment. In particular, the method comprises administering to a subject in need thereof an effective amount of (2-(4-methoxyphenyl)quinolin-4-yl)(piperidin-2-yl)methanol (also as "NSC23925") or a pharmaceutically acceptable salt thereof, thereby reducing drug resistance in the subject.

In certain embodiments, (2-(4-methoxyphenyl)quinolin-4-yl)(piperidin-2-yl)methanol or a pharmaceutically acceptable salt thereof is administered to the subject in a dose that is lower than the dose required to produce cytotoxicity in the subject. One embodiment provides that (2-(4-methoxyphenyl)quinolin-4-yl)(piperidin-2-yl)methanol or a pharmaceutically acceptable salt thereof is administered to the subject at a dose at least 10 fold lower than that is required to produce cytotoxicity in the subject. Another embodiment provides that (2-(4-methoxyphenyl)quinolin-4-yl)(piperidin-2-yl)methanol or a pharmaceutically acceptable salt thereof is administered at a dose at least 50 fold lower than that is required to produce cytotoxicity in the subject being treated.

Some embodiments provide that (2-(4-methoxyphenyl)quinolin-4-yl)(piperidin-2-yl)methanol or a pharmaceutically acceptable salt thereof is administered to a subject in need at a dose between about 0.001 mg/Kg and about 100 mg/Kg.

Certain embodiments provide that the method further comprises administering to a subject in need an anti-cancer therapeutic agent. (2-(4-Methoxyphenyl)quinolin-4-yl)(piperidin-2-yl)methanol or a pharmaceutically acceptable salt thereof and the anti-cancer therapeutic agent can be administered simultaneously. Alternatively, (2-(4-methoxyphenyl)quinolin-4-yl)(piperidin-2-yl)methanol or a pharmaceutically acceptable salt thereof and the anti-cancer therapeutic agent can be administered to the subject sequentially. In these instances, some embodiments provide that (2-(4-methoxyphenyl)quinolin-4-yl)(piperidin-2-yl)methanol or a pharmaceutically acceptable salt thereof is administered to the subject prior to the administration of the anti-cancer agent. Other embodiments provide that (2-(4-methoxyphenyl)quinolin-4-yl)(piperidin-2-yl)methanol or a pharmaceutically acceptable salt thereof is administered after the administration of the anti-cancer agent.

The aforementioned anti-cancer therapeutic agent can be, but is not limited to, asparaginase, bleomycin, calcein-AM, carboplatin, carmustine, chlorambucil, cisplatin, colaspase, cyclophosphamide, cytarabine, dacarbazine, dactinomycin, daunorubicin, docetaxel, doxorubicin (adriamycine), epirubicin, etoposide, ET-743 (also as "yondelis" or "trabectedin"), 5-fluorouracil, gemcitabine, hexamethylmelamine, hydroxyurea, ifosfamide, irinotecan, leucovorin, lomustine, mechlorethamine, 6-mercaptopurine, mesna, methotrexate, mitomycin C, mitoxantrone, paclitaxel (also as "taxol"), predniso lone, prednisone, procarbazine, raloxifen, rhodamine-123, streptozocin, tamoxifen, thioguanine, topotecan, vinblastine, vincristine, vindesine, or zalypsis.

In one embodiment, the anti-cancer therapeutic agent is paclitaxel, doxorubicin, docetaxel, calcein-AM, daunorubicin, gemcitabine, rhodamine-123, ET-743, vincristin or zalypsis. In other embodiments, the anti-cancer therapeutic agent is a cytotoxic drug selected from the group consisting of anthracyclines, vinca alkaloids and taxanes.

In certain embodiments, the cancer treatment which the subject is undergoing or has undergone is a treatment for a cancer of the breast, respiratory tract, brain, reproductive organs, digestive tract, urinary tract, eye, liver, skin, head and neck, thyroid, parathyroid or a distant metastasis of a solid tumor. One example of the distant metastasis of a solid tumor is sarcoma.

The invention also provides a kit for use to reduce drug resistance in a subject undergoing cancer treatment. The kit includes an effective amount of (2-(4-methoxyphenyl)quinolin-4-yl)(piperidin-2-yl)methanol or a pharmaceutically acceptable salt thereof, and instructions for administering the (2-(4-methoxyphenyl)quinolin-4-yl)(piperidin-2-yl)methanol or a pharmaceutically acceptable salt thereof, wherein the afore-mentioned effective amount is at a dose lower than the dose required to produce cytotoxicity in the subject, and instructions for use.

Certain embodiments provide that the dose of (2-(4-methoxyphenyl)quinolin-4-yl)(piperidin-2-yl)methanol or a pharmaceutically acceptable salt thereof in the kit is at least 10 fold less than the dose required to produce cytotoxicity in the subject. One embodiment provides that the kit includes (2-(4-methoxyphenyl)quinolin-4-yl)(piperidin-2-yl)methanol or a pharmaceutically acceptable salt thereof at a dose of between about 0.001 mg/Kg and about 100 mg/Kg. Other embodiments also provide that the kit includes an anti-cancer therapeutic agent. Examples of the anti-cancer therapeutic agent are listed above.

Another aspect of the invention provides a method for treating cancer in a subject. The method includes a) identifying a subject undergoing cancer treatment and having developed or being susceptible to develop drug resistance; and b) administering to the subject an effective amount of (2-(4-methoxyphenyl)quinolin-4-yl)(piperidin-2-yl)methanol or a pharmaceutically acceptable salt thereof, wherein the effective amount is sufficient to reduce drug resistance in the subject; thereby treating the subject for cancer In certain embodiments, the method involves discontinuation of the cancer treatment which the subject is undergoing or has undergone. Such cancer treatment can be discontinued prior to the administration of (2-(4-methoxyphenyl)quinolin-4-yl)(piperidin-2-yl)methanol or a pharmaceutically acceptable salt thereof. Alternatively, the cancer treatment is discontinued after the administration of (2-(4-methoxyphenyl) quinolin-4-yl)(piperidin-2-yl)methanol or a pharmaceutically acceptable salt thereof.

In certain embodiments, the subject in need is also administered a subsequent cancer treatment after the afore-mentioned cancer treatment is discontinued and (2-(4-methoxyphenyl)quinolin-4-yl)(piperidin-2-yl)methanol or a pharmaceutically acceptable salt thereof is administered. The subsequent cancer treatment can be the same as or different from the discontinued cancer treatment.

Certain embodiments also provide that an additional effective amount of (2-(4-methoxyphenyl)quinolin-4-yl)(piperidin-2-yl)methanol or a pharmaceutically acceptable salt thereof is administered to the subject after the administration of the subsequent cancer treatment. Such additional effective amount of (2-(4-methoxyphenyl)quinolin-4-yl)(piperidin-2-yl)methanol or a pharmaceutically acceptable salt thereof can be administered, for example, between within a hour to about 6 months after the subsequent cancer treatment has been introduced to treat the subject.

In one embodiment, the method of invention comprises repeatedly administering to the subject in need an additional effective amount of (2-(4-methoxyphenyl)quinolin-4-yl)(piperidin-2-yl)methanol or a pharmaceutically acceptable salt thereof after the administration of the subsequent cancer treatment.

In certain embodiments, the cancer treatment in accordance with the invention is selected from the group of consisting of surgery, chemotherapy, radiation therapy, immunotherapy and monoclonal antibody therapy.

In another aspect, the invention also provides a pharmaceutical composition that includes an amount of (2-(4-methoxyphenyl)quinolin-4-yl)(piperidin-2-yl)methanol or a pharmaceutically acceptable salt thereof effective for reducing drug resistance in a subject undergoing cancer treatment.

In certain embodiments, the effective amount of (2-(4-methoxyphenyl)quinolin-4-yl)(piperidin-2-yl)methanol or a pharmaceutically acceptable salt thereof included in the pharmaceutical composition is at a dose lower than that is required to produce cytotoxicity in the subject. One embodiment provides that the effective amount of (2-(4-methoxyphenyl) quinolin-4-yl)(piperidin-2-yl)methanol or its pharmaceutically acceptable salt thereof is at a dose at least 10 fold lower than that is required to produce cytotoxicity in the subject.

In one embodiment, the composition further includes an anti-cancer therapeutic agent. Examples of the anti-cancer therapeutic agent are discussed supra.

In one embodiment, the anti-cancer therapeutic agent is paclitaxel, doxorubicin, docetaxel, calcein-AM, daunorubicin, gemcitabine, rhodamine-123, ET-743, vincristin or zalypsis.

Yet another aspect of the invention provides a method of identifying a compound for use in reducing drug resistance in a subject undergoing cancer treatment. The method comprises a) screening compounds for their inhibitory activities on drug resistant cell lines through high-throughput assay; b) identifying a lead compound; and c) evaluating the ability of the lead compound to inhibit or modulate the function of P-glycoprotein (Pgp). One embodiment provides that the lead compound is further evaluated for its ability to inhibit MRP1 function. A separate embodiment provides that the subject method further comprises evaluating the ability of the lead compound to affect BCRP mediated drug resistance.

The invention also provides methods for designing, evaluating and identifying a compound that is capable of reducing drug resistance in a subject undergoing a cancer treatment. Other embodiments of the invention are disclosed infra.

DETAILED DESCRIPTION OF THE INVENTION

Figure 1:
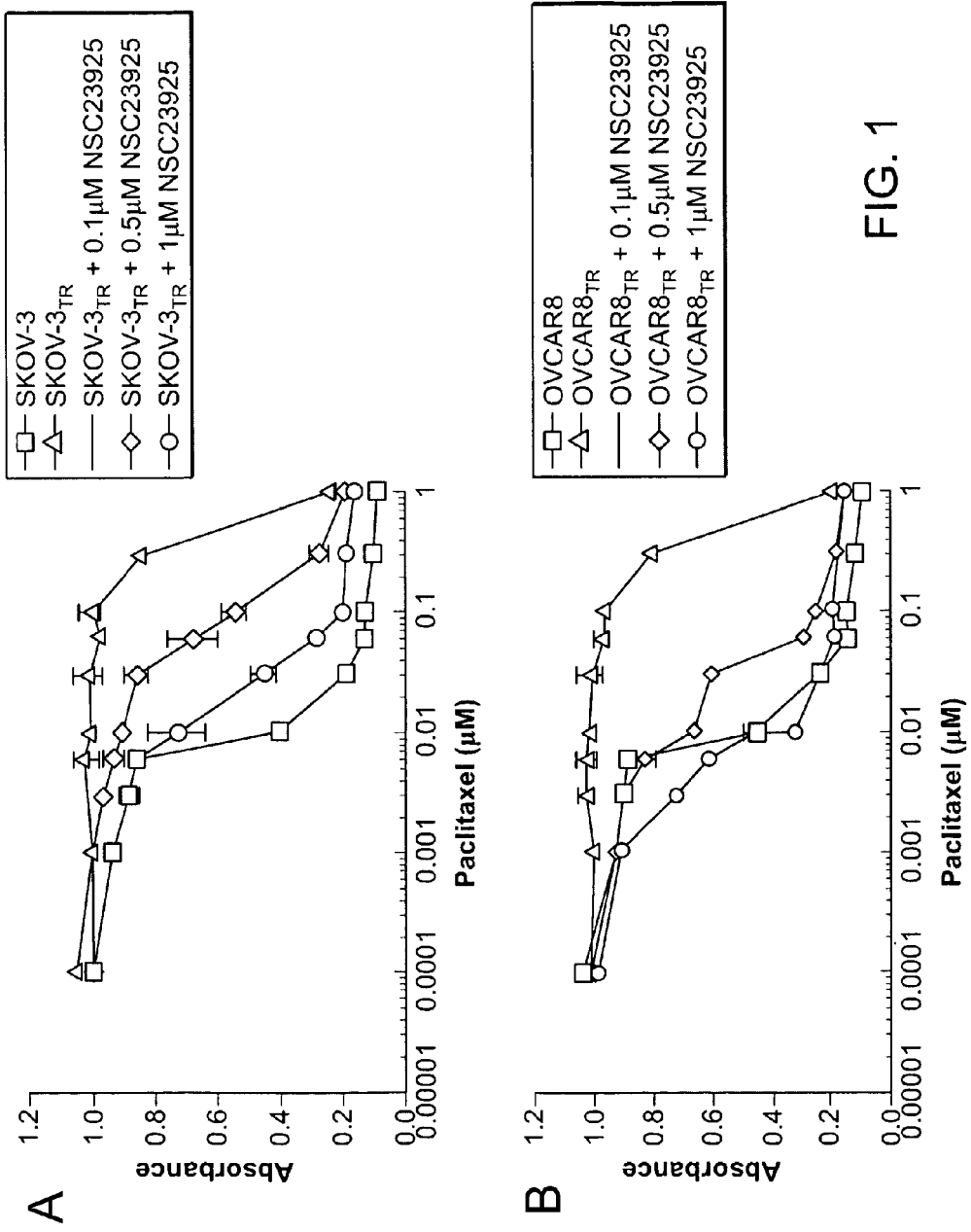
FIGS. 1 (*a-b*) are graphs that depict the effects of NSC23925 on drug sensitivity in ovarian cancer cells; 1(a) depicts the effects of NSC23925 on sensitive (SKOV-3) and resistant (SKOV-3$_{TR}$) cells; 1(b) depicts the effects of NSC23925 on sensitive (OVCAR8) and resistant (OVCAR8$_{TR}$) cells. Cells were treated with the paclitaxel and NSC23925 in RPMI1640 complete media at the indicated concentrations. The relative sensitivity of each line to paclitaxel was determined by MTT assay, as described below in the Examples section, 6 days post treatment. A: Reversal of paclitaxel resistance by NSC23925 in SKOV-3$_{TR}$ cells. B: Reversal of paclitaxel resistance by NSC23925 in OVCAR8$_{TR}$ cells.
Figure 2A:
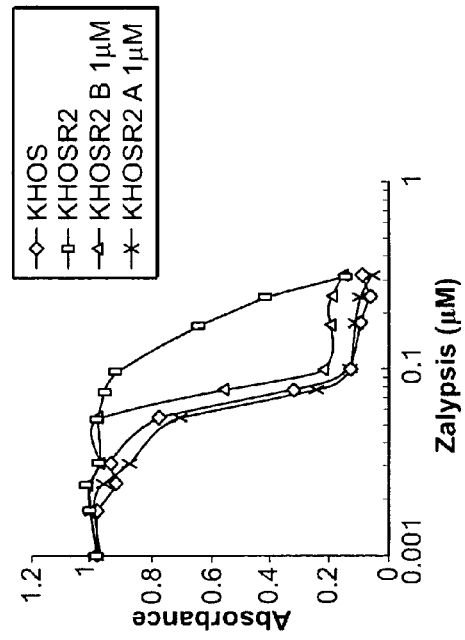
FIGS. 2 (a-c) show the effects of NSC23925 on drug sensitivity in various osteosarcoma cells: 2(a) depicts the effects of NSC23925 on sensitive (KHOS) and ET-743-resistant (KHOSR2) cells; 2(b) depicts the effects of NSC23925 on sensitive (KHOS) and zalypsis-resistant (KHOSR2) cells; 2(c) depicts the effects of NSC23925 on sensitive (KHOS) and doxorubicin-resistant (KHOSR2) cells.
Figure 2B:
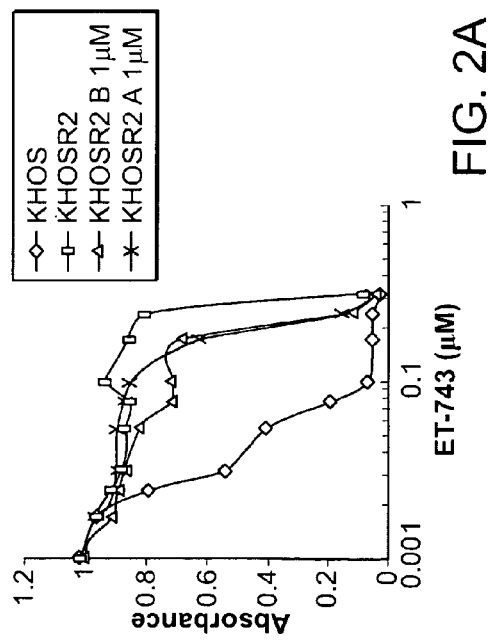
Figure 2C:
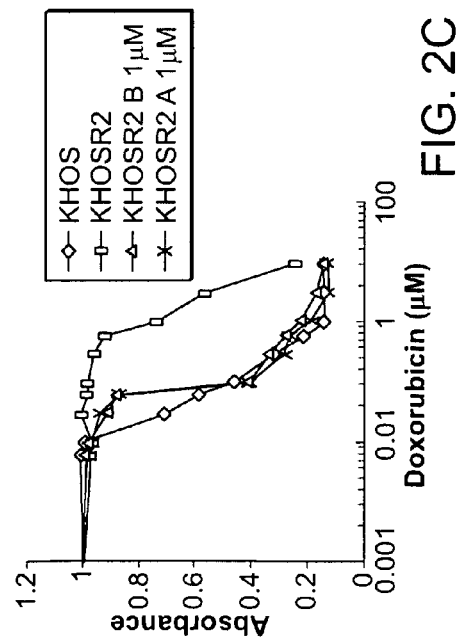

The invention provides for the identification of compounds useful in reducing drug resistance in a subject undergoing a cancer treatment. The compounds identified herein are capable of reversing Pgp-mediated drug resistance in the Pgp-overexpressing cell lines. In particular, the compound identified is (2-(4-Methoxyphenyl)quinolin-4-yl)(piperidin-2-yl)methanol (also as "NSC23925") or a pharmaceutically acceptable salt thereof.

The invention is based, at least in part, on the discovery on the underlying molecular rationales for the phenomenon of drug resistance in cancer treatment. The overexpression of Pgp is believed to be a common cause of intrinsic cellular mechanisms associated with the development of drug resistance. Pgp belongs to the ABC (ATP binding cassette) superfamily of transporter proteins, and it acts as an energy-dependent drug efflux pump, preventing adequate intracellular accumulation of a broad range of cytotoxic drugs for cell kill. Accordingly, it is believed in the art that reduction or elimination of the Pgp expression in the drug-resistant cancer cells in cancer treatment is necessary to let the cells become sensitive to cytotoxic drugs.

In accordance with the invention, a high-throughput cellular screening on the NCI Diversity Set library has been used to identify compounds for reducing drug resistance in a subject undergoing cancer treatment. The assay utilized was based on restoration of paclitaxel-mediated cytotoxicity in Pgp-expressing, drug resistant human ovarian cancer cells (SKOV-3$_{TR}$). To investigate the potential of the compound to reverse drug resistance, SKOV-3$_{TR}$ cells were treated with different compounds in the presence (1 µM) or absence of paclitaxel (i.e. "taxol"). This concentration of paclitaxel is lethal to SKOV-3 cells, but does not affect the growth of SKOV-3$_{TR}$ cells. The assay also employed 96-well microplate technology with standard cell survival assay.

After having screened 2000 compounds, the present inventors have unexpectedly discovered that (2-(4-methoxyphenyl)quinolin-4-yl)(piperidin-2-yl)methanol (also identified as "NSC23925") is capable of reducing (or even reversing) drug resistance in cancer cells. In particular, it was discovered that (2-(4-methoxyphenyl)quinolin-4-yl)(piperidin-2-yl)methanol increases the intracellular accumulation of the Pgp substrates (e.g. calcein AM, Rhodamine-123, paclitaxel and doxorubicin) by enhancing the uptake and/or decreasing the efflux of these Pgp substrates in drug resistant cells. Further studies show that (2-(4-methoxyphenyl)quinolin-4-yl)(piperidin-2-yl)methanol stimulates ATPase activity in a dose-dependent manner, which is required for the proper function of Pgp. Although ATPase activity is closely associated with the function of Pgp, and an increase in the ATPase activity does not necessarily lead to an enhancement in Pgp function.

For instance, verapamil is a Pgp reversal agent, but it stimulates the ATPase activity of Pgp. In contrast, (2-(4-methoxyphenyl)quinolin-4-yl)(piperidin-2-yl)methanol does not inhibit the expression level of Pgp. These results indicate that (2-(4-methoxyphenyl)quinolin-4-yl)(piperidin-2-yl)methanol is capable of reducing (or reversing) drug resistance in cancer cells for chemotherapy drugs by directly inhibiting the function of Pgp.

I. DEFINITIONS

Before further description of the invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either an anti-cancer therapeutic agent or with a pharmaceutically-acceptable carrier, or both. The compound of the invention can be administered prior to the administration of the anti-cancer therapeutic agent, simultaneously with the agent, or after the administration of the agent. Furthermore, the compound of the invention can also be administered in a pro-drug form which is converted into its active metabolite, or more active metabolite in vivo.

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The term "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In an embodiment, a suitable biological composition or biological sample is a red blood cell suspension. In some embodiments, the blood cell suspension includes mammalian blood cells. The blood cells can be obtained from a human, a non-human primate, a dog, a cat, a horse, a cow, a goat, a sheep or a pig. In certain embodiments, the blood cell suspension includes red blood cells and/or platelets and/or leukocytes and/or bone marrow cells.

The term "cytotoxicity" and "toxicity" refers to the quality of being toxic to cells. A toxic agent can be a chemical substance, an immune cell or some types of venom.

The term "cancer" refers to a class of diseases in which a group of cells display uncontrolled growth, invasion, and metastasis. The term is meant to include, but not limited to, a cancer of the breast, respiratory tract, brain, reproductive organs, digestive tract, urinary tract, eye, liver, skin, head and neck, thyroid, parathyroid or a distant metastasis of a solid tumor. Some specific examples of cancers include, but not limited to, breast cancer, bladder cancer, colon and rectal cancer, colorectal cancer, cutaneous melanoma, endometrial cancer, kidney cancer, lung cancer, ovarian cancer, pancreatic cancer, osteosarcoma, prostate cancer, lymphoma, leukemia, skin cancer, thyroid cancer and sarcoma.

The term of "chemotherapy" refers to treatment of disease by chemicals that kill cells, specifically those of micro-organisms or cancer. In the present application, this term refers to anti-cancer therapeutic agents used to treat cancer or the combination of these drugs into a cytotoxic standardized treatment regimen.

The term "chiral" refers to molecules which have the property of non-superimposability of the mirror image partner, while the term "achiral" refers to molecules which are superimposable on their mirror image partner.

The term "a cytotoxic drug" (or "cytotoxics") used in the present application refers to a drug that inhibit and combat the development of tumors.

The term "diastereomers" refers to stereoisomers with two or more centers of dissymmetry and whose molecules are not mirror images of one another.

The term "distant metastasis" means the spread of a disease from one organ or part to another non-adjacent organ or parts via lymph or blood. For the purposes of the present application, the term "metastasis" refers to cancer cells that can spread from a primary tumor, enter lymphatic and blood vessels, circulate through the bloodstream, and settle down to grow within normal tissues elsewhere in the body.

The term "drug resistance" means the reduction in effectiveness of a drug in curing a disease or improving a patient's symptoms. In particular, the term in the present application refers to the phenomenon that cancer cells are resisting the effect of chemotherapeutic agents or of an anti-cancer treatment. When a cell is resistant to more than one drug, it is said to be multidrug resistant (also as "MDR").

The term "effective amount" includes an amount effective, at dosages and for periods of time necessary, to achieve the desired result, e.g., sufficient to reduce the severity or the incidence of drug resistance in cancer treatment. An effective amount of compound of the invention may vary according to factors such as the state of the drug resistance developed, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 100 mg/Kg body weight. Certain examples are about 0.01 to 30 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the drug resistance developed, previous cancer treatments, the general health and/or age of the subject, and other diseases present. Moreover, treatment of a subject with a therapeutically effective amount of a compound of the invention can include a single treatment or, can include a series of treatments. One example is that a subject is treated with a compound of the invention at a dosage in the range of between about 0.001 to about 100 mg/Kg body weight, once per day. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "immunotherapy" refers to a therapy to treat cancer by modulating the immune system of the subject being treated. In certain embodiments, immunotherapy used in cancer treatment aims to stimulate tumor specific adaptive immune responses within the body of the subject.

The language "improved biological properties" refers to any activity inherent in a compound of the invention that enhances its effectiveness in vivo. In one embodiment, this term refers to any qualitative or quantitative improved therapeutic property of a compound of the invention, such as reduced cytotoxicity.

The term "modulate" refers to an increase or decrease, e.g., in the ability of a compound to inhibit activity of a target in response to exposure to a compound of the invention, including such that a desired end result is achieved, e.g., a therapeutic result, in a subject (e.g., animal, human).

The term "monoclonal antibody therapy" refers to a therapy using monoclonal antibodies (or mAb) to specifically target cancer cells. The goal is to stimulate the subject's immune system to attack the malignant tumor cells and the prevention of tumor growth by blocking specific cell receptors. Examples of this therapy include radioimmunotherapy, antibody-directed enzyme prodrug therapy, drug and gene therapy using immuno-liposomes. Certain therapeutic monoclonal antibodies include, but are not limited to, alemtuzumab, bevacizumab, cetuximab, efalizumab, ibritumomab tiuxetan, 111in-capromab, imciromab, panitumumab, gemtuzumab ozogamicin, rituximab, tositumomab, and trastuzumab.

The term "obtaining" as in "obtaining a compound" to reduce the severity or incidence of drug resistance delineated herein and is intended to include purchasing, synthesizing or otherwise acquiring the compound.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Particular prodrug moieties include propionoic acid esters and acyl esters. Prodrugs which are converted to active forms through other mechanisms in vivo are also included.

The language "a prophylactically effective amount" of a compound refers to an amount of a compound of the invention herein which is effective, upon single or multiple dose administration to the subject, in reducing the severity or incidence of drug resistance in cancer treatment.

The term "radiation therapy" (or "radiotherapy") refers to the medical use of ionizing radiation as part of cancer treatment to control malignant cells. Certain examples provide that a radiotherapy is used for curative or adjuvant cancer treatment.

The language "reducing drug resistance" is intended to include reducing the incidence or severity of the phenomenon of drug resistance a subject which has developed or is susceptible to develop in a therapy. In some instances, the language is meant to include reversing (partially or completely) the drug resistance in the subject.

The language "reduced toxicity" is intended to include a reduction in any undesired side effect elicited by a compound of the invention when administered in vivo.

The term "pharmaceutically acceptable salt" refers to a relatively non-toxic, inorganic or organic acid addition salt of a compound of the invention. For example, see S. M. Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of the compounds of the invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate. Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The term "solvate" is meant to encompass a complex of a solvent and a compound of the invention in the solid state. Exemplary solvates would include, but are not limited to, complexes of a compound of the invention with ethanol or methanol. Hydrates are a specific form of solvate wherein the solvent is water.

The term "susceptible to develop drug resistance" is meant to include subjects at risk of developing drug resistance in cancer treatment. For example, subjects have symptoms of developing drug resistance in cancer treatment, subjects have prior medical history of development of drug resistance or related symptom thereof in a cancer or even non-cancer related treatment, or subjects having a family member having development of drug resistance or related symptom thereof in a cancer or even non-cancer related treatment.

The phrases "systemic administration," "administered systemically", "peripheral administration" and "administered peripherally" as used herein mean the administration of a compound of the invention(s), composition, drug or other material, such that it enters the subject's system and, thus, is subject to metabolism and other like processes, for example, subcutaneous administration.

The term "treating" or "treatment" is used conventionally, e.g., the management or care of a subject for the purpose of combating, alleviating, reducing, relieving, improving the condition of, etc., of a disease or disorder, delineated herein.

II. COMPOUNDS

As set forth above, the invention provides compounds capable of reducing drug resistance in a subject undergoing cancer treatment. In one aspect, the compound is (2-(4-Methoxyphenyl)quinolin-4-yl)(piperidin-2-yl)methanol (also as "NSC23925") or a pharmaceutically acceptable salt thereof.

In one embodiment, a compound of the invention is a compound with the chemical structure as follows:

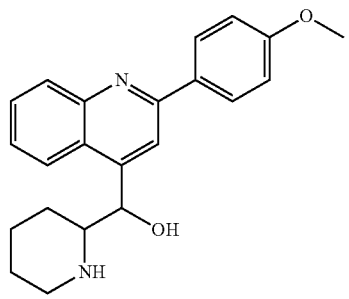

NSC23925
(2-(4-methoxyphenyl)quinolin-4-yl)(piperidin-2-yl)methanol

The invention also provides the pharmaceutically acceptable salts, esters, hydrates, solvates, clathrates, polymorphs, and prodrugs of (2-(4-Methoxyphenyl)quinolin-4-yl)(piperidin-2-yl)methanol thereof.

The compounds of the invention may contain one or more asymmetric centers and thus occur as racemates and racemic mixtures, single enantiomers, individual diastereomers and diastereomeric mixtures. All such isomeric forms of these compounds are expressly included in the invention. The compounds of this invention may also be represented in multiple tautomeric forms, in such instances, the invention expressly includes all tautomeric forms of the compounds described herein. All such isomeric forms of such compounds are expressly included in the invention. All crystal forms of the compounds described herein are expressly included in the invention.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

Methods of obtaining a compound of the invention include purchasing, synthesizing or otherwise acquiring the compound. Synthesizing a compound of the invention is within the means of chemists of ordinary skill in the art. Methods for optimizing reaction conditions, if necessary minimizing competing by-products, are known in the art. The methods may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

III. USES AND METHODS

The invention provides a method for using a compound of the invention and compositions thereof, to reduce (the incidence or severity of) drug resistance in a subject undergoing cancer treatment. Compounds of this invention can be utilized to reduce (e.g. reverse) drug resistance in cancer cells. In certain embodiments, a compound of the invention reduces (e.g. reverses) drug resistance through inhibiting the function of Pgp.

The method comprises administering to a subject in need thereof an effective amount of a compound of the invention, thereby reducing drug resistance in the subject undergoing cancer treatment. The effective amount of a compound of the invention is an amount sufficient to reduce (the incidence or severity of) drug resistance in the subject. An effective amount of a compound of this invention can be provided in one or a series of administrations (or doses). The effective amount of a compound of this invention is generally determined by the physician on a case-by-case basis and is within the skill of one in the art.

In certain embodiments, the compound of the invention is administered to the subject at a dose that is lower than the dose required to produce cytotoxicity in the subject. One embodiment provides that the compound of the invention is administered to the subject at a dose at least 10 fold lower than that is required to produce cytotoxicity in the subject. A separate embodiment provides that the compound is administered at a dose at least 50 fold lower than that is required to produce cytotoxicity in the subject being treated.

Another aspect of the invention provides a method for treating cancer in a subject by using a compound of the invention. The method includes a) identifying a subject undergoing cancer treatment and having developed or being susceptible to develop drug resistance; and b) administering to the subject an effective amount of a compound of the invention, wherein the effective amount is sufficient to reduce drug resistance in the subject; and the method thereby treats cancer in a subject. Such an effective amount may be an amount effective therapeutically and/or prophylactically.

Determination of a therapeutically effective amount or a prophylactically effective amount of the compound of the invention, can be readily made by the physician or veterinarian (the "attending clinician"), as one skilled in the art, by the use of known techniques and by observing results obtained under analogous circumstances. The amount (or dose) may be varied depending upon the requirements of the subject in the judgment of the attending clinician; the severity of the condition being treated and the particular compound being employed. In determining the effective amount for the purpose of the invention, a number of factors are considered by the attending clinician, including, but not limited to: the age, sex and weight of the subject being treated; the specific cancer involved; pharmacodynamic characteristics of the particular anti-cancer agent used and its mode and route of administration; the desired time course of treatment; the species of mammal; its size, age, and general health; the degree of or involvement or the severity of the cancer; the response of the individual subject; the degree or severity of the drug resistance symptom in the subject; the mode of administration; the bioavailability characteristics of the preparation administered; the dose regimen selected; the kind of concurrent treatment (i.e., the interaction of the compound of the invention with other co-administered therapeutics); and other relevant circumstances.

Further, the identification of those subjects undergoing cancer treatment and having developed or being susceptible to develop drug resistance is well within the ability and knowledge of one skilled in the art. Certain of the methods for identification of subjects which are at risk of developing drug resistance which can be treated by the subject method are appreciated in the medical arts, such as prior medical history, family history, and the presence of risk factors associated with the development of the phenomenon in the subject. A clinician skilled in the art can readily identify such candidate subjects, by the use of, for example, clinical tests, physical examination and medical/family history screen.

While using a compound of the invention to treat cancer in a subject, the methods sometimes involve discontinuation of the cancer treatment which the subject has undergone or is undergoing. In certain embodiments, the subject in need is then administered a subsequent cancer treatment after the afore-mentioned cancer treatment has been discontinued and a compound of the invention has been administered. This subsequent cancer treatment can be the same as or different from the discontinued cancer treatment.

Certain embodiments also provide that an additional effective amount of a compound of the invention is administered to the subject after the administration of the subsequent cancer treatment. In certain embodiments, the method of invention comprises repeatedly administering to the subject in need an additional effective amount of a compound of the invention after administration of the subsequent cancer treatment.

An attending physician or veterinarian can readily make a determination on when to administer the additional effective amount of the compound of this invention after the administration of the subsequent cancer treatment. Such determination can be made based on subjective and/or objective standards. Certain examples provide that the additional effective amount of a compound of the invention is administered between within a hour to about 6 months after the subsequent cancer treatment has been introduced to treat the subject. Specific examples may include the administration of the additional effective amount of the compound of the invention 1 day, 1 week, 2 weeks, one month, or six months after the administration of the subsequent cancer treatment. The extent or severity of the drug resistance symptoms may be determined periodically throughout treatment. For example, the extent or severity of the drug resistance symptoms may be checked every few hours, days or weeks to assess the efficacy of the treatment. A decrease in extent or severity of the drug resistance symptoms indicates that the treatment is efficacious. The method described may be used to screen or select subjects that may benefit from treatment with a compound of the invention.

The cancer treatment includes, but is not limited to, surgery, chemotherapy, radiation therapy, immunotherapy or monoclonal antibody therapy.

A method of assessing the efficacy of the subject method to treat cancer in a subject includes determining the pre-treatment extent of a cancer by methods well known in the art and then administering to the subject an effective amount of a compound of the invention. After an appropriate period of time after the administration of the subject method (e.g., 1 day, 1 week, 2 weeks, one month, six months), the extent/severity of the drug resistance is determined again. The modulation (e.g., decrease) of the extent or severity of the drug resistance in the subject indicates efficacy of the treatment. The extent or severity of the drug resistance may be determined periodically throughout treatment. For example, the extent or severity of the drug resistance may be checked every few hours, days or weeks to assess the further efficacy of the treatment. Further, a decrease in extent or severity of the cancer also indicates that the treatment is efficacious. The method described may be used to screen or select subjects that may benefit from treatment with a compound of the invention.

Cancers, for the purpose of the invention, include a class of diseases in which a group of cells display uncontrolled growth, invasion, and/or metastasis. Cancer mentioned herein may be but is not limited to, e.g., a cancer of breast, respiratory tract, brain, reproductive organs, digestive tract, urinary tract, eye, liver, skin, head and neck, thyroid, parathyroid or a distant metastasis of a solid tumor. In certain embodiments, cancers also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumor.

Cancers of the male reproductive organs include, but are not limited to prostate and testicular cancer. Cancers of the female reproductive organs include, but are not limited to endometrial, cervical, ovarian, vaginal, and vulvar cancer, as well as sarcoma of the uterus.

Cancers of the digestive tract include, but are not limited to anal, colon, colorectal, esophageal, gallbladder, gastric, pancreatic, rectal, small-intestine, and salivary gland cancers.

Cancers of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell.

Lymphomas include, but are not limited to, AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyo sarcoma.

Leukemias include, but are not limited to acute myeloid leukemia, acute lymphoblastic leukemia, chronic lymphocytic leukemia, chronic myelogenous leukemia, and hairy cell leukemia.

These diseases or disorders have been well characterized in humans, but also exist with a similar etiology in other mammals.

Another aspect of the invention is to use a compound of the invention in the treatment or prevention in a subject of a disease, disorder or symptom thereof delineated herein.

IV. COMBINATION THERAPY

A compound of the invention can be used alone or in combination with an additional therapeutic agent to treat such diseases delineated herein. Determination on such an additional therapeutic agent suitable to be combined with a compound of the invention can be readily made by the skilled artisan. For example, the additional agent can be a therapeutic agent art-recognized as being useful to treat the disease or condition being treated by the compound of the invention. The additional agent also can be an agent that imparts a beneficial attribute to the therapeutic composition e.g., an agent that affects the viscosity of the composition.

It should further be understood that the combinations encompassed by the invention are those combinations useful for their intended purpose. The agents set forth below are illustrative for purposes and not intended to be limited. The combinations, which are part of this invention, can be the compounds of the invention and at least one additional agent selected from the lists below. The combination can also include more than one additional agent, e.g., two or three additional agents if the combination is such that the formed composition can perform its intended function.

Certain combinations provide that the additional agent is an anti-cancer therapeutic agent. Such an anti-cancer therapeutic agent and a compound of the invention can be administered simultaneously. Alternatively, the compound of the invention and the anti-cancer therapeutic agent can be administered to the subject sequentially. Some embodiments provide that the compound of the invention is administered to the subject prior to the administration of the anti-cancer agent. Other embodiments provide that the compound of the invention is administered to the subject after the administration of the anti-cancer agent.

The anti-cancer therapeutic agent may be, but is not limited to, asparaginase, bleomycin, calcein-AM, carboplatin, carmustine, chlorambucil, cisplatin, colaspase, cyclophosphamide, cytarabine, dacarbazine, dactinomycin, daunorubicin, docetaxel, doxorubicin (adriamycine), epirubicin, etoposide, ET-743, 5-fluorouracil, gemcitabine, hexamethylmelamine, hydroxyurea, ifosfamide, irinotecan, leucovorin, lomustine, mechlorethamine, 6-mercaptopurine, mesna, methotrexate, mitomycin C, mitoxantrone, paclitaxel, prednisolone, prednisone, procarbazine, raloxifen, rhodamine-123, streptozocin, tamoxifen, thioguanine, topotecan, vinblastine, vincristine, vindesine, or zalypsis.

Proteosome inhibitors (e.g., MG-132), hydroxyureas (e.g., Hydrea or hydroxycarbamide) or kinase inhibitors (e.g., GLEEVEC) can also be used in combination with the compounds of the invention. Certain therapeutic monoclonal antibodies can also be used with a compound of the invention. Such monoclonal antibodies include, but not limited to, alemtuzumab, bevacizumab, cetuximab, efalizumab, ibritumomab tiuxetan, 111in-capromab, imciromab, panitumumab, gemtuzumab ozogamicin, rituximab, tositumomab, and trastuzumab.

Certain embodiments of the invention provide that the anti-cancer therapeutic agent is paclitaxel, doxorubicin, docetaxel, calcein-AM, daunorubicin, gemcitabine, rhodamine-123, ET-743, vincristin or zalypsis. Separately, the anti-cancer therapeutic agent may be a cytotoxic drug selected from the group consisting of anthracyclines, vinca alkaloids and taxanes.

Non-limiting examples of other therapeutic agents that can be used in combination may include, e.g., antiangiogenesis agents, anti-proliferative agents, DNA-RNA transcription regulators, DNA synthesis inhibitors, enzyme inhibitors/activators, HSP-90 inhibitors, microtubule inhibitors, gene regulators, antibodies, etc. A list of the additional therapeutic agents that may be used in combination with a compound of the invention can be found in *Harrison's Principles of Internal Medicine,* 17th Edition, Eds. T. R. Harrison et al. McGraw-Hill N.Y., NY; and the Physicians Desk Reference 62nd Edition 2008, Oradell N.J., Medical Economics Co., the complete contents of which are expressly incorporated herein by reference.

Examples of antiangiogenesis agents include, but not limited to, angiostatin k1-3 human, dl-α-difluoromethylornithine hydrate hydrochloride, endostatin, endostatin murine, fumagillin, genistein, minocycline hydrochloride, silibinin, silymarin, staurosporine, su 5416, and thalidomide.

Examples of anti-proliferative agents include, but not limited to, 25-hydroxycholesterol, 7β-hydroxycholesterol, aloe-emodin, apigenin, berberine, caffeine, dichloro-methylene-diphosphonic acid disodium salt, emodin, HA 14-1, hyperforin, N-acetyl-d-sphingosine, N-hexanoyl-d-sphingosine, parthenolide, β-ionone, and trans-cinnamaldehyde.

Examples of DNA-RNA transcription regulators include, but not limited to, 5,6-dichlorobenzimidazole, 1-β-d-ribofuranoside, actinomycin d, homoharringtonine, and idarubicin hydrochloride.

Examples of DNA synthesis inhibitors include, but not limited to, amethopterin, 2-fluoroadenine-9-β-D-arabinofuranoside, 5-fluoro-5'-deoxyuridine, 6-mercaptopurine, 6-thioguanine, aminopterin, cytosine-β-D-arabinofuranoside, ganciclovir, and hydroxyurea.

Examples of enzyme activators/inhibitors include, but not limited to, forskolin, (–)-deguelin, (–)-depudecin, camptothecin, 2-imino-1-imidazolidineacetic acid, 2-propylpentanoic acid, 7-ethyl-10-hydroxycamptothecin, DL-aminoglutethimide, apicidin and etoposide.

Examples of HSP-90 inhibitors include, but not limited to, 17-(allylamino)-17-demethoxygeldanamycin, geldanamycin, and rifabutin.

Examples of microtubule inhibitors include, but not limited to, colchicine, dolastatin, nocodazole, podophyllotoxin, rhizoxin, vinblastine, and vinorelbine hydrate ditartrate salt.

Examples of gene regulators, include, but not limited to, 13-cis-Retinoic acid, 4-Hydroxytamoxifen, 5-Aza-2'-deoxycytidine, 5-Azacytidine, 9-cis-Retinoic acid, Cholecalciferol, ciglitizone, cyproterone acetate, epitestosterone, flutamide, GW9662, glycyrrhizic acid ammonium salt, melatonin, mifepristone, procainamide hydrochloride, raloxifene, retinoic acid, retinol, tamoxifen, tetradecylthioacetic acid, and troglitazone.

Examples of antibodies include, but not limited to, alemtuzumab, bevacizumab, cetuximab, efalizumab, ibritumomab tiuxetan, 111in-capromab, imciromab, panitumumab, gemtuzumab ozogamicin, rituximab, tositumomab, and trastuzumab.

The compounds of the invention and the additional therapeutic agent(s) may be administered to the subject in the same pharmaceutical composition or in different pharmaceutical compositions (at the same time or at different times).

Another aspect of the invention provides the use of a compound of the invention, alone or together with one or more additional therapeutic agents in the manufacture of a medicament, either as a single composition or as separate dosage forms, for treatment or prevention in a subject of a disease, disorder or symptom set forth herein.

V. DOSAGES

Suitable dosages of a compound of the invention can be empirically determined by an administering physician. Standard texts, such as Remington: The Science and Practice of Pharmacy, 17th edition, Mack Publishing Company, and the Physician's Desk Reference, each of which are incorporated herein by reference, can be consulted to prepare suitable compositions and doses for administration. A determination of the appropriate dosage is within the skill of one in the art given the parameters for use described herein.

Some embodiments provide that a dose of a compound of the invention is expected to vary from about 0.001 mg/kg of body weight to about 100 mg/Kg. Treatment can be initiated with smaller dosages. The dosage may then be increased by small increments until the optimum effect under the circumstances is reached. For convenience, the total dosage may be divided and administered in portions during the administration period if desired.

The dosages may be varied depending upon the requirements of the subject in the judgment of the attending clinician; the severity of the condition being treated and the particular compound being employed. In determining the effective amount or dose, and the prophylactically effective amount or dose, a number of factors are considered by the attending clinician, including, but not limited to: the age, sex and weight of the subject being treated; the specific cancer involved; pharmacodynamic characteristics of the particular anti-cancer agent used and its mode and route of administration; the desired time course of treatment; the species of mammal; its size, age, and general health; the degree of or involvement or the severity of the cancer; the response of the individual subject; the degree or severity of the drug resistance symptom in the subject; the mode of administration; the bioavailability characteristics of the preparation administered; the dose regimen selected; the kind of concurrent treatment (i.e., the interaction of the compound of the invention with other co-administered therapeutics); and other relevant circumstances.

The dosage of a compound of the invention can vary from about 0.01 mg to about 5,000 mg per day. In some instances, the dosage varies from about 100 mg to about 4000 mg per day, or about 1000 mg to about 3000 mg per day. Ascertaining dosage ranges is well within the skill of one in the art. In certain embodiments, the dosage of a compound of the invention can range from about 0.001 to about 100 mg/Kg of body weight. Certain ranges are about 0.01 to about 30 mg/kg body weight, about 0.1 to 20 mg/kg body weight, about 1 to 10 mg/kg, about 2 to 9 mg/kg, about 3 to 8 mg/kg, about 4 to 7 mg/kg, or about 5 to 6 mg/kg body weight. Such dosages may vary, for example, depending on whether multiple administrations are given, tissue type and route of administration, the condition of the individual, the desired objective and other factors known to those of skill in the art. Administrations can be conducted frequently, for example, on a regular daily or weekly basis, until a desired, measurable parameter is detected, such as diminution of disease symptoms. Administration can then be diminished, such as to a biweekly or monthly basis

VI. FORMULATIONS AND DOSAGE FORMS

This invention also provides pharmaceutical compositions containing an effective amount of a compound of the invention. The pharmaceutical compositions may also comprise a pharmaceutically acceptable carrier or diluent. These compositions can be utilized to achieve the desired pharmacological effect by administration to a subject in need thereof. A subject, for the purpose of this invention, is a mammal, including a human, in need of treatment for the particular condition or disease.

In certain embodiments, the effective amount of a compound of the invention included in the pharmaceutical composition is at a dose lower than that is required to produce cytotoxicity in the subject. One embodiment provides that the effective amount of a compound of the invention is at a dose at least 10 fold lower than that is required to produce cytotoxicity. The effective amount is effective to reduce the severity or incidence of dug resistance in a subject undergoing cancer treatment, as described previously.

A pharmaceutically acceptable carrier is advantageously a carrier that is relatively non-toxic and innocuous to a subject at concentrations consistent with effective activity of the active ingredient so that any side effects ascribable to the carrier do not vitiate the beneficial effects of the active ingredient. An effective amount of a compound is advantageously that amount which reduces drug resistance in the subject undergoing cancer treatment. The compounds of the invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, or vaginally.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, a compound of the invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of the invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

Compounds of the invention may also be administered parenterally, in other words, subcutaneously, intravenously, intraocularly, intrasynovially, intramuscularly, or interperitoneally, as injectable dosages of the compound in advantageously a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

Parenteral compositions of the invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation includes ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

Compositions of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the invention employs transdermal delivery devices ("patches"). Such transdermal patches may be used to provide continuous or discontinuous infusion of the compounds of the invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)—Part-1" PDA Journal of Pharmaceutical Science & Technology 1999, 53(6), 324-349; and Nema, S. et al, "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

Acidifying agents (examples include but are not limited to acetic acid, citric acid, fumaric acid, hydrochloric acid, nitric acid);

Alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

Adsorbents (examples include but are not limited to powdered cellulose and activated charcoal);

Aerosol propellants (examples include but are not limited to carbon dioxide, $CCl_2F_2$, $F_2ClC-CClF_2$ and $CClF_3$)

Air displacement agents (examples include but are not limited to nitrogen and argon);

Antifungal preservatives (examples include but are not limited to benzoic acid, butylparaben, ethylparaben, methylparaben, propylparaben, sodium benzoate);

Antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

Antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

Binding materials (examples include but are not limited to block polymers, natural and synthetic rubber, polyacrylates, polyurethanes, silicones, polysiloxanes and styrene-butadiene copolymers);

Buffering agents (examples include but are not limited to potassium metaphosphate, dipotassium phosphate, sodium acetate, sodium citrate anhydrous and sodium citrate dihydrate);

Carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

Chelating agents (examples include but are not limited to edetate disodium and edetic acid)

Colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

Clarifying agents (examples include but are not limited to bentonite);

Emulsifying agents (examples include but are not limited to acacia, cetomacrogol, cetyl alcohol, glyceryl monostearate, lecithin, sorbitan monooleate, polyoxyethylene 50 monostearate);

Encapsulating agents (examples include but are not limited to gelatin and cellulose acetate phthalate);

Flavorants (examples include but are not limited to anise oil, cinnamon oil, cocoa, menthol, orange oil, peppermint oil and vanillin);

Humectants (examples include but are not limited to glycerol, propylene glycol and sorbitol);

Levigating agents (examples include but are not limited to mineral oil and glycerin);

Oils (examples include but are not limited to arachis oil, mineral oil, olive oil, peanut oil, sesame oil and vegetable oil);

Ointment bases (examples include but are not limited to lanolin, hydrophilic ointment, polyethylene glycol ointment, petrolatum, hydrophilic petrolatum, white ointment, yellow ointment, and rose water ointment);

Penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

Plasticizers (examples include but are not limited to diethyl phthalate and glycerol);

Solvents (examples include but are not limited to ethanol, corn oil, cottonseed oil, glycerol, isopropanol, mineral oil, oleic acid, peanut oil, purified water, water for injection, sterile water for injection and sterile water for irrigation);

Stiffening Agents (examples include but are not limited to cetyl alcohol, cetyl esters wax, microcrystalline wax, paraffin, stearyl alcohol, white wax and yellow wax);

Suppository Bases (examples include but are not limited to cocoa butter and polyethylene glycols (mixtures));

Surfactants (examples include but are not limited to benzalkonium chloride, nonoxynol 10, oxtoxynol 9, polysorbate 80, sodium lauryl sulfate and sorbitan mono-palmitate);

Suspending Agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

Sweetening Agents (examples include but are not limited to aspartame, dextrose, glycerol, mannitol, propylene glycol, saccharin sodium, sorbitol and sucrose);

Tablet anti-adherents (examples include but are not limited to magnesium stearate and talc);

Tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

Tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

Tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

Tablet direct compression excipients (examples include but are not limited to dibasic calcium phosphate);

Tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

Tablet glidants (examples include but are not limited to colloidal silica, corn starch and talc);

Tablet lubricants (examples include but are not limited to calcium stearate, magnesium stearate, mineral oil, stearic acid and zinc stearate);

Tablet/capsule opaquants (examples include but are not limited to titanium dioxide);

Tablet polishing agents (examples include but are not limited to carnuba wax and white wax);

Thickening agents (examples include but are not limited to beeswax, cetyl alcohol and paraffin);

Tonicity agents (examples include but are not limited to dextrose and sodium chloride);

Viscosity increasing agents (examples include but are not limited to alginic acid, bentonite, carbomers, carboxymethylcellulose sodium, methylcellulose, polyvinyl pyrrolidone, sodium alginate and tragacanth); and Wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the invention can be illustrated as follows:

Sterile IV Solution: A 5 mg/mL solution of a compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of a compound of this invention
5 mg/mL sodium carboxymethylcellulose
4 mg/mL TWEEN 80
9 mg/mL sodium chloride
9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

The pharmaceutical compositions of this invention may further include additional therapeutic agent as previously discussed. Certain examples provide that additional therapeutic agent is an anti-cancer therapeutic agent. Such an anti-cancer agent may be, for example, asparaginase, bleomycin, calcein-AM, carboplatin, carmustine, chlorambucil, cisplatin, colaspase, cyclophosphamide, cytarabine, dacarbazine, dactinomycin, daunorubicin, docetaxel, doxorubicin (adriamycine), epirubicin, etoposide, ET-743, 5-fluorouracil, gemcitabine, hexamethylmelamine, hydroxyurea, ifosfamide, irinotecan, leucovorin, lomustine, mechlorethamine, 6-mercaptopurine, mesna, methotrexate, mitomycin C, mitoxantrone, paclitaxel, prednisolone, prednisone, procarbazine, raloxifen, rhodamine-123, streptozocin, tamoxifen, thioguanine, topotecan, vinblastine, vincristine, vindesine, or zalypsis. In certain embodiments, the additional therapeutic agent is paclitaxel, doxorubicin, docetaxel, calcein-AM, daunorubicin, gemcitabine, rhodamine-123, ET-743, vincristin or zalypsis.

When a compound of the invention is administered as pharmaceuticals, to humans and animals, it can be given per se or as a pharmaceutical composition containing, for example, 0.1 to 99.5% (or 0.5 to 90%) of active ingredient in combination with a pharmaceutically-acceptable carrier.

Regardless of the route of administration selected, the compound of the invention, which may be used in a suitable hydrated form, and/or the pharmaceutical compositions of the invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular subject, composition, and mode of administration, without being toxic to the subject. An exemplary dose range is from about 0.001 to about 100 mg/kg per day. Other examples for the dose range are discussed supra. An advantageous dose of the compound of the invention is the maximum that a subject can tolerate and not develop serious side effects.

VII. KITS

The invention also provides kits for treating diseases delineated herein. A typical kit of this invention includes a compound, a pharmaceutical formulation or a combination described in this document, and instructions for use. The instructions for use may include information on dosage, method of delivery, storage of the kit, etc. Certain embodiments provide that the kit includes instructions for administering the compound, formulation or combination of this invention.

A kit may include instructions and/or information for identification of a subject in need for treatment. In certain embodiments, the kit may include instructions to treat a subject suffering from or susceptible to drug resistance in a cancer treatment. Sometimes, a kit may include instructions to treat or prevent cancer.

The effective amount of the compound included in the kit is as above discussed. Typically, the effective amount of a compound of this invention is at a dose lower than the dose required to produce cytotoxicity in the subject. Certain embodiments provide that the effective amount of a compound of the invention included in the kit is at least 10 fold less than the amount required to produce cytotoxicity in the subject. Certain embodiments provide that the kit includes a compound of the invention at a dose of between about 0.001 mg/Kg and about 100 mg/Kg.

Some embodiments provide that the kit further includes an additional therapeutic agent as previously discussed. In some examples, the additional therapeutic agent is an anti-cancer therapeutic agent as discussed supra.

The kits may also include, reagents, for example, test compounds, buffers, media (e.g., cell growth media), cells, etc. Test compounds may include known compounds or newly discovered compounds, for example, combinatorial libraries of compounds.

Kits of the invention can further comprise devices that are used to administer a compound of the invention. Examples of such devices include, but are not limited to, intravenous cannulation devices, syringes, drip bags, patches, topical gels, pumps, containers that provide protection from photodegradation, autoinjectors, and inhalers.

Kits of the invention can also comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

VIII. METHOD TO IDENTIFY DRUG RESISTANT INHIBITORS

This invention also provides a method for identifying a compound for use in reducing drug resistance in a subject undergoing cancer treatment. The method comprises a) screening compounds for their inhibitory activities on drug resistant cells line through high-throughput assay; b) identifying a lead compound; and c) evaluating the ability of said lead compound to inhibit or modulate the function of P-glycoprotein (Pgp). In certain embodiments, the method also includes evaluating the ability of the lead compound to inhibit MRP1 function. In a separate embodiment, the method further includes evaluating the ability of the lead compound to affect BCRP mediated drug resistance.

In certain embodiments, the high-throughput assay is a cell-based high-throughput screening assay. In one embodiment, the cell-based high-throughput assay is utilized for the identification of novel drug resistance inhibitors to reduce (or reverse) drug resistance in a subject undergoing a cancer treatment.

The cell-based high-throughput assay is designed to screen the small molecular compound library and to identify novel drug resistant inhibitor. Certain embodiments include evaluation on the effects of a small molecular compound on SKOV-$3_{TR}$ drug resistant cell lines. Separate embodiments provide that the subject method comprise evaluation the effects of a compound on U-2OS$_{TR}$, OVCAR8$_{TR}$, MCF-7$_{TR}$, SW480$_{TR}$, MCF-7$_{DR}$ or OVCAR5$_{GR}$ drug resistant cell lines. In certain embodiments, the cell lines are resistant to paclitaxel, doxorubicin, or gemcitbine.

Certain examples provide that the assay is conducted in one control plate and one experimental plate. This design allows plate-to-plate comparisons. The control plate (plate A) is only treated with a compound being evaluated. Thus, plate A is used to evaluate cytotoxicity of the compound itself, and to exclude a compound that is lethal to the cells in the absence of an anti-cancer drug. The experiment plate as a second plate (plate B) is treated with both the compound and an anti-cancer drug. One embodiment is that the anti-cancer drug is paclitaxel. Another embodiment provides that paclitaxel is at a sublethal dose for the SKOV-3$_{TR}$ cell line. An example is that paclitaxel is at a concentration of 0.1 µM. Through this assay, a compound that is associated with cells surviving in plate A and cells dying in plate B is identified as "a hit" or "lead compound".

Certain embodiments of the subject method also comprises validating an identified hit (or a lead compound) for reducing drug resistance in additional drug resistant cell lines. Examples of the additional drug resistant cell lines include ovarian, breast, colon, sarcoma drug resistance cell lines. In a separate embodiment, the compound may be also evaluated for its inhibitory effect on cytotoxic drug activity in non-Pgp expression parental cell lines.

The cell-based high-throughput screening assay as above discussed significantly extends the previous techniques in the art. Compared to the previous techniques, this assay has the advantages in identifying small-molecule hits that are accessible to intracellular targets, active with intact signaling pathways, and in the presence of serum.

Without wishing to be bound by any theory, a compound identified through the method of invention is capable of reducing or modulating drug resistance in a subject undergoing cancer treatment. In certain embodiments, the compound identified through the present method demonstrates specificity in modulating or reducing drug resistance in cancer cell lines of the subject being treated.

EXAMPLES

The invention now being generally described will be more readily understood by reference to the following examples, which are included merely for purposes of illustration of certain aspects and embodiments of the present invention and are not intended to limit the invention.

Example 1

Database of Small Molecules

The Structural Diversity Set is a library of approximately 2,000 small molecules derived from the almost 140,000 compounds available on plates through the National Cancer Institute (NCI). Detailed information on the selection, structures, and activities of these diversity set compounds can be found on the NCI Developmental Therapeutics Program web site (http://dtp.nci.nih.gov).

Example 2

High-Throughput Drug Cytotoxicity Assay

Drugs, Cell Lines, Antibodies.
DMSO were purchase from Sigma-Aldrich (St. Louis, Mo.). Paclitaxel (also as "Taxol") Paclitaxel, doxorubicin, and cisplatin were obtained through unused residual clinical material provided by the pharmacy at the Massachusetts General Hospital. ET-743 (trabectidin, Yondelis) and PM00104 (Zalypsis) were supplied by PharmaMar (Spain). The stock solution of drugs were prepared according to the drug specifications and stored at −20° C.

The paclitaxel-resistant U-2OS$_{TR}$, SKOV-3$_{TR}$, OVCAR8$_{TR}$, MCF-7$_{TR}$ and SW480$_{TR}$ lines as well as doxorubicin resistant MCF-7$_{DR}$ and gemcitbine resistant OVCAR5$_{GR}$ cell lines were established as previously reported. Duan Z, Lamendola D E, Duan Y, Yusuf R Z, Seiden M V (2005) Description of paclitaxel resistance-associated genes in ovarian and breast cancer cell lines. Cancer Chemother Pharmacol 55: 277-285; Duan Z, Choy E, Jimeno J M, Cuevas Cdel M, Mankin H J, et al. (2009) Diverse cross-resistance phenotype to ET-743 and PM00104 in multi-drug resistant cell lines. Cancer Chemother Pharmacol 63: 1121-1129; Lamendola D E, Duan Z, Yusuf R Z, Seiden M V (2003) Molecular description of evolving paclitaxel resistance in the SKOV-3 human ovarian carcinoma cell line. Cancer Res 63: 2200-2205; and Duan Z, Feller A J, Toh H C, Makastorsis T, Seiden M V (1999) TRAG-3, a novel gene, isolated from a taxol-resistant ovarian carcinoma cell line. Gene 229: 75-81. Briefly, these drug resistant cell lines were selected over a period of six to ten months by continuous culture in media containing step-wise increases in paclitaxel. The human osteosarcoma cell line U-205, KHOS, human uterine sarcoma cell line MESSA and its doxorubicin selected drug resistant cell line MES-SA/Dx5, human ovarian cancer cell line SKOV-3, human breast cancer cell line MCF-7, human colon cancer cell line SW480, human non-small cell lung cancer cell line H-69 and it's doxorubicin selected drug resistant cell line H-69AR were obtained from the American Type Tissue Collection (Rockville, Md.).

Dr. Efstathios Gonos (Institute of Biological Research & Biotechnology, Athens, Greece) provided the doxorubicin resistant U-2OS R2 (referred in the text below as U-2OS$_{DR}$), KHOS R2 cell lines [25]. Dr. Stephen. Howell (The University of California Medical Center, San Diego) provided the cisplatin-resistant ovarian cancer IGROV1cp and 2008 cp70 cell lines. Dr. Erasmus Schneider (Wadsworth Center, Albany) provided the mitoxantrane resistant breast cancer MCF-7/MX cell line. Dr. Katia Scotlandi (Institute Orthopedics Rizzoli, Italy) provided ET-743 resistant TC-ET 6 nM and TC-ET 12 nM cell lines.

The Pgp1 monoclonal antibody C219 was purchased from Signet (Dedham, Mass.). The mouse monoclonal antibody to MRP1 and MTT reagent were purchased from Sigma-Aldrich (St. Louis, Mo.). The monoclonal antibody to BCRP antibody was purchased from Chemicon (Temecula, Calif.). The Goat anti-rabbit-HRP and goat anti-mouse-HRP were purchased from Bio-Rad (Hercules, Calif.). SuperSignal® West Pico Chemiluminescent Substrate was purchased from PIERCE (Rockford, Ill.).

Cell Culture.
All the cell lines were cultured in RPMI 1640 (Invitrogen, Carlsbad, Calif.) supplemented with 10% fetal bovine serum, 100-units/ml penicillin and 100 µg/ml streptomycin (Invitrogen). Cells were incubated at 37° C. in 5% $CO_2$-95% air atmosphere and passaged when near confluent monolayers were achieved using trypsin-EDTA solution. Drug-resistant cell lines were periodically cultured in the respective drug to confirm their drug resistance characteristics. Cells were free on mycoplasma contamination as tested by MycoAlert(R) *Mycoplasma* Detection Kit from Cambrex (Rockland, Me.).

Assay.
Screening conditions in drug resistant cells were optimized in 96-well plates for optimal growth conditions, small molecular compound and drug concentration and assay times prior to screening. On day 1, drug resistant cells were seeded at 2×10⁴ cells/well on 96-well plates and labeled with plates A, B, and incubated for 24 hr at 37° C. On day 2, plate A was treated with a test compound at 1 µM to each well without paclitaxel; Plate B was treated with both a test compound and paclitaxe at specifically prescribed concentrations. From day 4 to day 6, fresh medium was replaced with necessity as described above and evaluated for cytotoxicity under the microscope. On Day 6, the number of viable cells was evaluated for cytotoxicity in any wells under the microscope manually and final results were determined via CELLTITER96™ AQ One Solution Cell Cytotoxicity Assay (Promega, Madison, Wis.) by a SPECTRAIVIAX.™ Microplate Spectrophotometer (Molecular Devices, Sunnyvale, Calif.).

The general format was designed for screening the small molecular compound library and identifying novel drug resistant inhibitor. These include evaluation of each small molecular compound through a well studied multidrug resistant cell line SKOV-3TR. The experiments were conducted in two control plates (A and B) and one experimental plate (C) to permit plate-to-plate comparisons (FIG. 1). The control plates (plate A and B) were used to evaluate cytotoxicity of paclitaxel and small molecular compound itself, and to exclude compound that were lethal to the cells in the absence of chemotherapy drug. Plate B was necessary because the goal of this study was to identify small molecular compound that can reverse drug resistance and not to determine cell toxicity. Therefore, one plate (plate B) was given only small molecular compound to confirm that the small molecule is not lethal in the absence of paclitaxel (a positive result is cell survival); Plate C was given both small molecular compound and 0.1 µM paclitaxel. This is typically a sublethal dose of paclitaxel for the SKOV-3TR cell line and a positive result would be cell death at 4-6 days. Small molecular compound that were associated with cell survival in plate A and plate B and death in plate C were identified as "hits" and selected for further study.

Only the compounds at 1 µM showed no cytotoxicity (without paclitaxel) to SKOV-$3_{TR}$ were selected for further study.

Results.

Figure 4A:
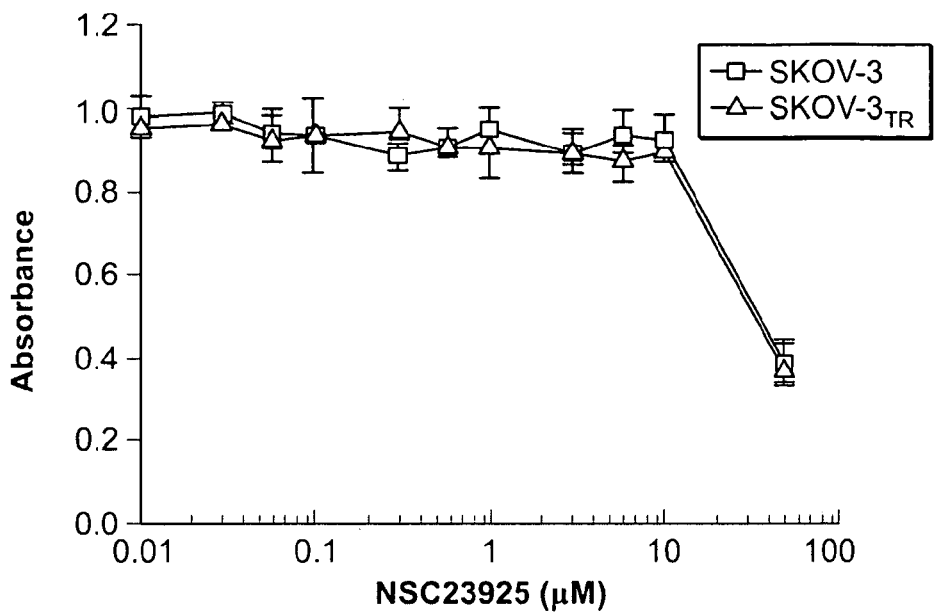
FIGS. 4(a-b) show that NSC23925 has no specific toxicity in SKOV3 and SKOV-3$_{TR}$ cell lines and OVCAR8 vs OVCAR8TR cell lines. Cells were treated with the NSC23925 in RPMI1640 complete media at the indicated concentrations. The relative sensitivity of each line to NSC23925 was determined by MTT assay. A: Nonspecific toxicity of NSC23925 on SKOV3 vs SKOV-3TR. B: Nonspecific toxicity of NSC23925 on OVCAR8 vs OVCAR8TR.
Figure 4B:
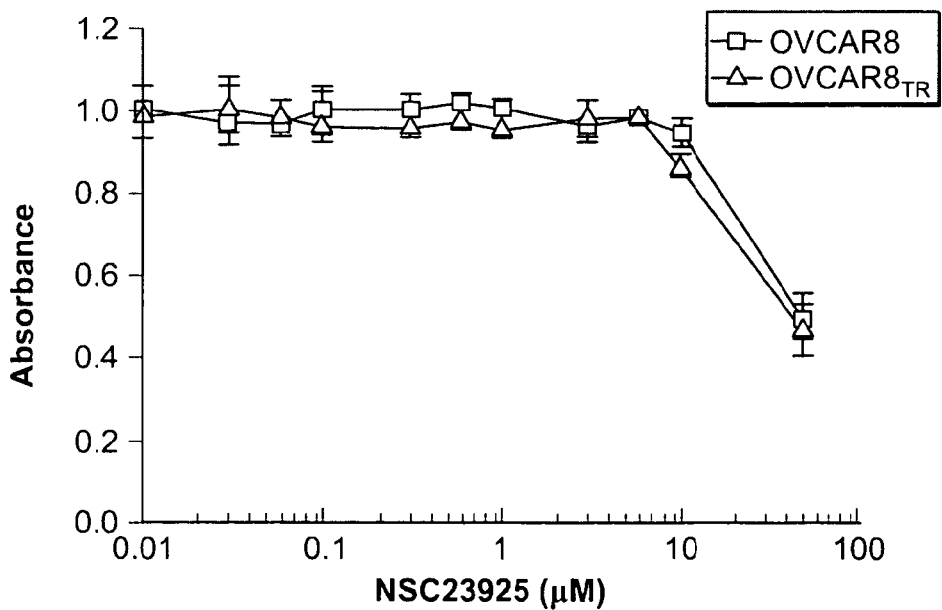

To determine whether NSC23925 is able to reverse drug resistance in other cancer cell lines, the effects of NSC23925 on several MDR cell lines using a variety of anti-cancer agents were evaluated. NSC23925 reverses chemoresistance in a wide variety of tumor types where MDR1 is highly expressed; these tumor types include the ovarian cancer cell lines SKOV-3TR and OVCAR8TR, breast cancer cell line MCF-7TR, and sarcoma cell lines MESSA/Dx5, KHOS R2, and U-2OSDR (representative data from SKOV-3TR, OVCAR8TR, and KHOS R2 shown in Table 1). Maximal reversal of MDR was typically seen in NSC23925 doses between 0.5 and 1 µM (FIG. 1). NSC23925 was highly active across the panel of cell lines and demonstrated significant reversal of chemoresistance when used in conjunction with paclitaxel, docetaxel, doxorubicin, daunorubicin, gemcitabine, vincristine, ET-743, or PM00104 (Table 2). The potency of NSC23925 was 10 to 50 fold greater than that of verapamil or CsA. Moreover, the presence of <5-10 µM of NSC23925 alone had no cytotoxic effect in the parental cell lines SKOV-3 and OVCAR8 which lack expression of Pgp1 (FIGS. 4A and 4B). Importantly, NSC23925 did not alter the cytotoxicity of cisplatin and methotrexate, both agents known to be unaffected by MDR1 mechanisms (Table 2). These results suggest that reversal of resistance was mostly attributable to the inhibition of Pgp1. Furthermore, other cell lines with non-Pgp1 mediated MDR mechanisms were tested (H69/AR cells that express MRP1, but not Pgp1, and MCF-7 MX cells that express BCRP, but not Pgp1) to evaluate the specificity of NSC23925. It was observed that NSC23925 was unable to reverse drug resistance in these non-Pgp1 expressing drug resistant cell lines, suggesting that NSC23925 activity is specific for Pgp1.

TABLE 1

Effect of NSC23925 Reversing Drug Resistance in Multidrug Resistant Cell Lines

|  | SKOV-3TRIC$_{50}$ (µM) | OVCAR8TR IC$_{50}$ (µM) | KHOSR2IC$_{50}$ (µM) |
|---|---|---|---|
| Paclitaxel | 0.310 ± 0.021 | 0.34 ± 0.032 | 0.21 ± 0.023 |
| Add NSC23925 0.1 µM | 0.302 ± 0.056 (1.03) | 0.127 ± 0.027 (2.7) | 0.16 ± 0.016 (1.3) |
| Add NSC23925 0.5 µM | 0.132 ± 0.047 (2.4) | 0.072 ± 0.046 (4.7) | 0.12 ± 0.032 (1.8) |
| Add NSC23925 1 µM | 0.037 ± 0.028 (8.4) | 0.028 ± 0.047 (12.1) | 0.06 ± 0.020 (3.5) |
| Doxorubicin | 22.34 ± 0.2 | 27.624 ± 0.256 | 10.34 ± 0.566 |
| Add NSC23925 0.1 µM | 16.52 ± 0.21 (1.4) | 12.35 ± 0.36 (2.3) | 7.364 ± 0.336 (1.4) |
| Add NSC23925 0.5 µM | 6.78 ± 0.16 (3.3) | 5.200 ± 0.471 (5.3) | 1.205 ± 0.461 (8.6) |
| Add NSC23925 1 µM | 1.94 ± 0.22 (11.5) | 1.216 ± 0.122 (23) | 0.292 ± 0.210 (35) |
| ET-743 | 0.004 ± 0.002 | 0.006 ± 0.002 | 0.175 ± 0.025 |
| Add NSC23925 0.1 µM | 0.005 ± 0.002 (0.8) | 0.005 ± 0.001 (1.2) | 0.145 ± 0.045 (1.2) |
| Add NSC23925 0.5 µM | 0.004 ± 0.001 (1) | 0.005 ± 0.001 (1.2) | 0.083 ± 0.039 (2.1) |
| Add NSC23925 1 µM | 0.004 ± 0.001 (1) | 0.007 ± 0.002 (0.9) | 0.054 ± 0.034 (3.2) |
| PM00104 | 0.006 ± 0.001 | 0.008 ± 0.002 | 0.143 ± 0.045 |
| Add NSC23925 0.1 µM | 0.005 ± 0.002 (1.2) | 0.008 ± 0.002 (1) | 0.113 ± 0.038 (1.3) |
| Add NSC23925 0.5 µM | 0.007 ± 0.001 (0.9) | 0.006 ± 0.002 (1.3) | 0.026 ± 0.014 (5.5) |
| Add NSC23925 1 µM | 0.005 ± 0.002 (1.2) | 0.005 ± 0.002 (1.6) | 0.008 ± 0.016 (17.9) |

IC$_{50}$ is concentration of drug (µM) that produced 50% inhibition of cell growth.
Results calculated from one experiment with triplicate wells.
± reflect SDEV (SD).
Numbers in parentheses represent fold-reversal of drug resistance

TABLE 2

Reverse Drug Resistance by NSC23925

| Decreased drug resistance | No effect |
|---|---|
| Paclitaxel | Cisplatin |
| Docetaxel | Carboplatin |
| Doxorubicin | Topotecan |
| Vincristine | Methotrexate |
| Daunorubicin | |
| Vincristine | |
| Gemcitabine | |
| ET-743 | |
| PM00104 | |

Example 3

Cytotoxicity Assay

Drug cytotoxicity was assessed in vitro using the MTT assay. SKOV-3 and SKOV-$3_{TR}$ cells were used herein. Briefly, 2×10³ cells per well were plated in 96-well plates in culture medium (RPMI 1640 supplemented with 10% fetal bovine serum and penicillin/streptomycin) containing increasing concentrations of drug. After 7 days of culture, 10 µl MTT (5 mg/ml in PBS, obtained from Sigma) were added to each well and the plates were incubated for 4 h. The resulting formazan product was dissolved with acid-isopropanol and the absorbance at a wavelength of 490 nm ($A_{490}$) was read on a SPECTRAmax® Microplate Spectrophotometer (Molecular Devices, Sunnyvale, Calif.). The absorbance values were normalized by assigning the value of the control line in the medium without drug to 1.0 and the value of the no cell control to 0. Experiments were performed in triplicate.

Results.

Figure 3:
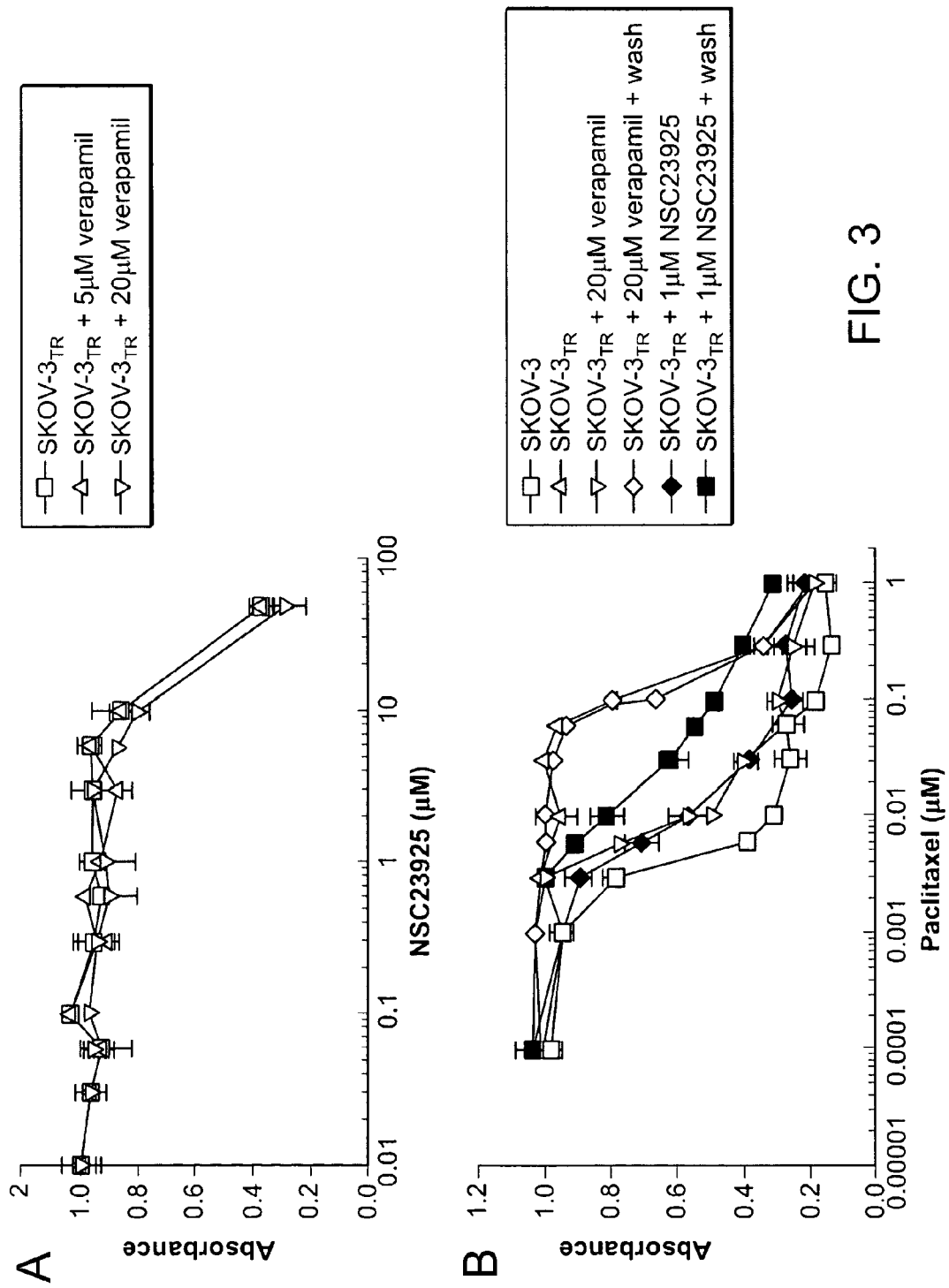
FIGS. 3(a-b) show the effects of NSC23925 and verapamil on drug sensitivity in SKOV-3 cells. A: Effect of verapamil on NSC23925 sensitivity in SKOV-3$_{TR}$ cells. SKOV-3$_{TR}$ cells were treated with different concentrations of NSC23925 alone or in combination with verapamil for 72 hours. Drug cytotoxicity was determined by MTT assay. B: Persistence of NSC23925 reverses paclitaxel resistance in SKOV-3$_{TR}$ cells after incubation and washout of NSC23925 or verapamil.

Cytotoxicity assay was performed on NSC23925 and the test results are depicted in FIG. 3. FIG. 3 demonstrates that NSC23925 is noncytotoxic at doses up to 10 µM in both sensitive and resistant cell lines. Results show that NSC23925 has an equally moderate inhibitory effect on the proliferation of both SKOV-3 and SKOV-$3_{TR}$ cells in a dose-dependent manner. Given the previous results showing that the required concentration of NSC23925 for full reversal of resistance in SKOV-$3_{TR}$ to various cytotoxic drugs is 0.5 µM to 2 µM, the instant results indicate that NSC23925 shows toxicity to human cell lines only at concentrations 10 to 50 fold greater than those required for complete reversal of drug resistance.

Although NSC23925 reversed Pgp1 mediated MDR in the nanomolar concentration range, NSC23925 was not cytotoxic by itself at doses up to 10 µM in both sensitive and resistant cell lines. At high concentrations, NSC23925 by itself is equally inhibitory on the proliferation of both SKOV-3 and SKOV-3TR and for OVCAR8 and OVCAR8TR cell lines in a dose-dependent manner (FIGS. 1A and 1B). IC50s were similar in matched cell lines that did and did not express Pgp1. The IC50 for NSC23925 is 8 µM in SKOV-3/SKOV-3TR and 25 µM in OVCAR8/OVCAR8TR cell lines, whereas the mean concentration of NSC23925 required for maximal reversal of resistance in SKOV-3TR or OVCAR8TR to cytotoxic drugs is 0.5 µM to 1 µM (FIGS. 1A and 1B). Thus, NSC23925 is cytotoxic at concentrations 10 to 50 fold greater than those required for maximal reversal of drug resistance. This indicates that overexpression of Pgp1 does not confer resistance to the cytotoxic effects of single agent NSC23925. These results also suggest that compounds like NSC23925 are not Pgp1 transport substrates. To confirm this, the effect of the Pgp1 inhibitor, verapamil, on NSC23925 sensitivity in Pgp1-overexpressing SKOV-3TR cells was determined. As expected, verapamil did not influence the cytotoxic effect of NSC23925 in SKOV-3TR cells (FIG. 3A). This data collectively demonstrates that NSC23925 itself is not a substrate of Pgp1, and Pgp1 does not confer resistance to the cytotoxic effects of NSC23925 in tumor cells. Also, NSC23925 is not subject to cross resistance with classical cytotoxic agents such as paclitaxel or doxorubicin. These results are of clinical significance because they suggest that NSC23925 is useful for the patients with tumors that have already developed MDR.

Example 4

Duration of Drug Resistance or MDR Reversal

Material.

Verapamil and DMSO were purchase from Sigma-Aldrich (St. Louis, Mo.). Paclitaxel and doxorubicin were obtained through unused residual clinical material provided by the pharmacy at the Massachusetts General Hospital. The stock solution of drugs were prepared according to the drug specifications and stored at −20° C. The paclitaxel-resistant SKOV-$3_{TR}$ cell lines were established as above discussed. All the cell lines were cultured as above discussed.

Experiment.

The experiment was performed as described by Dantzig et al. In brief, $8\times10^5$ SKOV-$3_{TR}$ Cells/ml were incubated for 24 h with or without a test compound or verapamil before being washed 3 times with growth medium. The cells were then incubated for 4 days with addition of varying concentrations of paclitaxel. Final results were determined by MTT assay as described above.

Results:

The ability of NSC23925 to inhibit Pgp1 mediated efflux and its duration of action were investigated using two MDR substrates, paclitaxel, doxorubicin, and two MDR cell lines SKOV-3TR and OVCAR8TR. It was observed that NSC23925 inhibits the efflux of both paclitaxel and doxorubicin from MDR cells and that the inhibitory effects of NSC23925 remains even when it was washed out from the efflux medium after overnight exposure (1 µM) (FIG. 3B). NSC23925 was effective at inhibiting Pgp1 mediated transport for at least 4 days after wash-out. In comparison, verapamil even after exposure to very high concentration (20 µM), displayed only a short duration (24 h) of inhibition (FIG. 3B). Similar results were obtained in OVCAR8TR cells (data not shown).

Example 5

Drug Efflux Assay

The VYBRANT™ multi-drug resistance assay kit (Invitrogen/Molecular Probes) was used to measure drug efflux properties of different resistant cell lines. This assay utilizes the fluorogenic dye calcein acetoxymethyl ester (calcein AM) as a substrate for efflux activity of Pgp1 or other membrane pump ABC proteins. Calcein AM is taken up by cells and hydrolyzed by cytoplasmic esterases to fluorescent calcein. Calcein AM is well retained in the cytosol. However, multidrug resistant cells expressing high levels of Pgp1 rapidly extrude non-fluorescent calcein AM from the plasma membrane, reducing accumulation of fluorescent calcein in the cytosol. Drug sensitive and resistant cells ($3\times10^5$) were cultured in 96-well plate for 24 hours and then incubated in 0.25 µM calcein AM in 150 µl total volume. After 30 minutes, the cells in plate were washed and centrifuged twice with 200 µl cold RPMI1640 culture medium, and cell fluorescence was measured at a wavelength of 490 nm ($A_{490}$) on a SPECTRAMAX™ Microplate Spectrofluorometer (Molecular Devices).

Results.

Figure 5B:
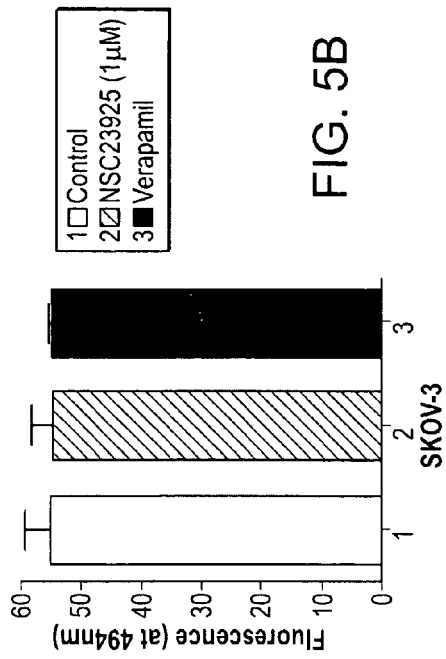
FIG. 5 depicts that effects of NSC23925, verapamil and on calcein-AM efflux from SKOV-3TR cells. Calcein-AM assay was optimized and performed using the VYBRANT™ multidrug resistance assay kit (Invitrogen/Molecular Probes) and SKOV-3$_{TR}$ cells. Cells were seeded at 50,000 cells/well (100 µl of culture medium) in a 96-well plate and incubated for 24 h. SKOV-3$_{TR}$ cells in triplicate were treated with NSC23925, verapamil for one hour and then incubated in calcein AM for 30 min. The cell fluorescence images were acquired by a fluorescence microscope (A, C) and quantities of fluorescence were measured in a SPECTRAmax Microplate Spectrofluorometer (B, D). The data were representative of one of three independent experiments. *, P<0.001.
Figure 5D:
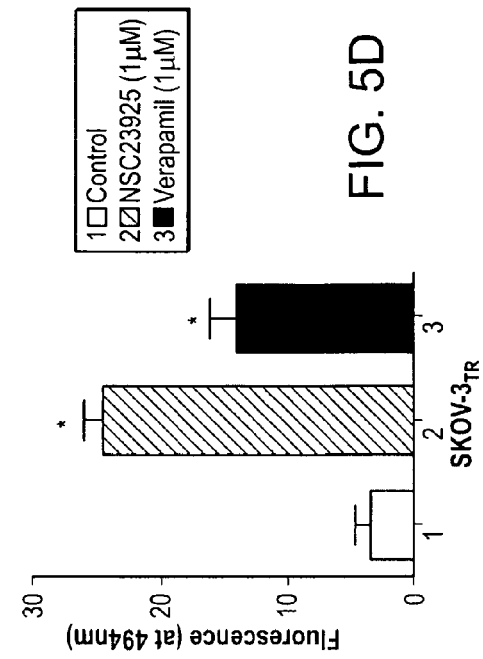
Figure 5A:
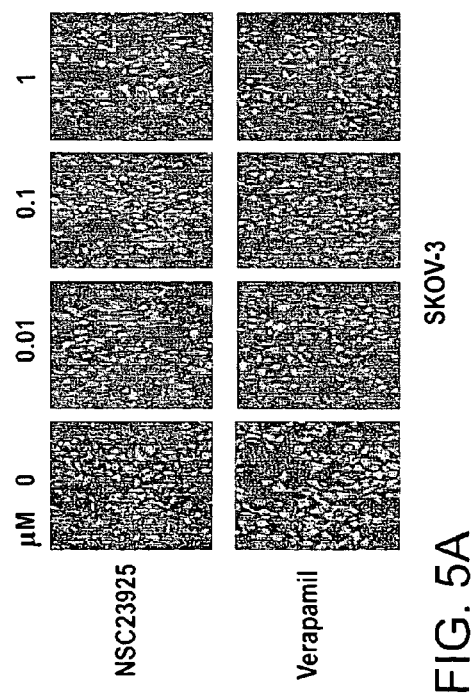
Figure 5C:
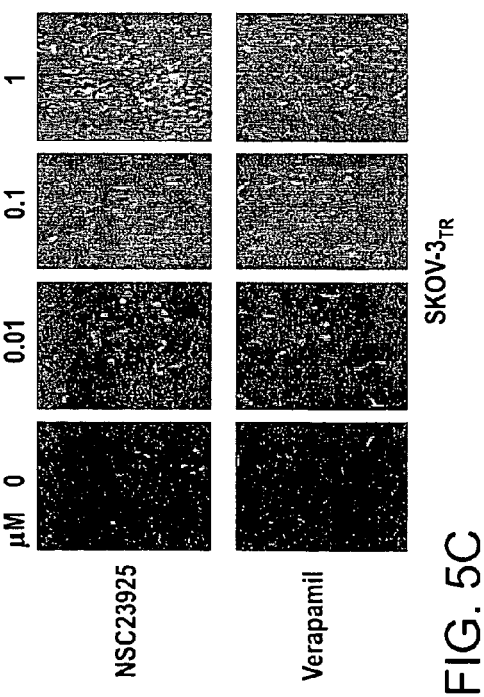
Figure 8:
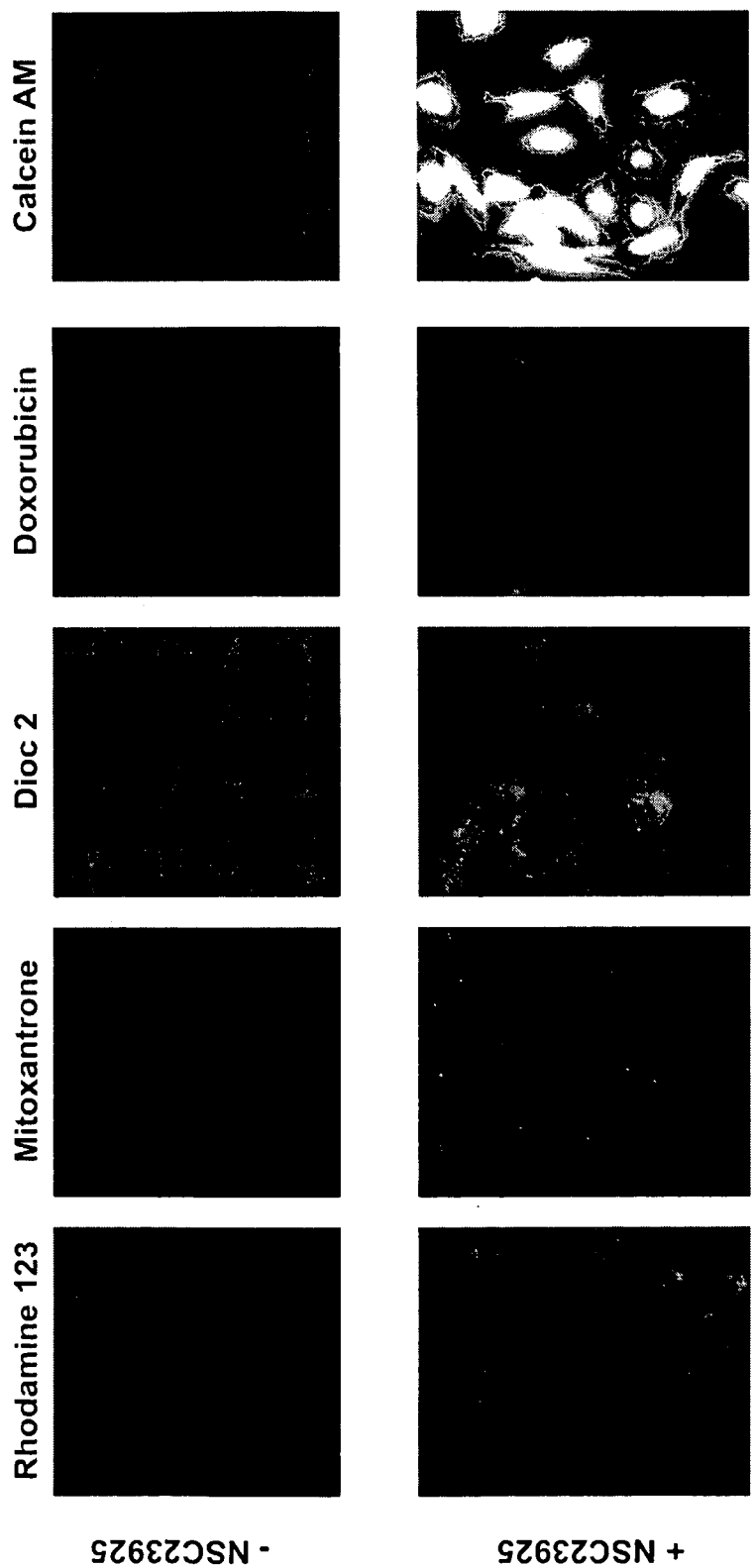
FIG. 8 depicts the increase in Pgp1 substrate accumulation in SKOV-3$_{TR\ by}$ NSC23925. Images of SKOV-3$_{TR}$ cells incubated with various fluorescent substrates of Pgp1 in the presence (bottom panel) and absence (top panel) of NSC23925. For visualization of effects of NSC23925 on the intracellular retention of rhodamine 123, mitoxantrone, Dioc2, doxorubicin, and calcein AM, 10,000 resistant cells were seeded on to Lab-Tek 8-well chamber slides on the day prior to the assay. SKOV-3$_{TR}$ cells were then incubated with either 1 µM rhodamine 123, 10 µM mitoxantrone, 0.1 µM Dioc2, 10 µM doxorubicin or 0.25 µM calcein AM either alone or in the presence of NSC23925 in RPMI 1640 media for one hour at 37° C. Image were acquired a Nikon Eclipse Ti-U fluorescence microscope (Nikon Corp.) equipped with a SPOT RT digital camera (Diagnostic Instruments, Inc., Sterling Heights, Mich.).
Figure 9:
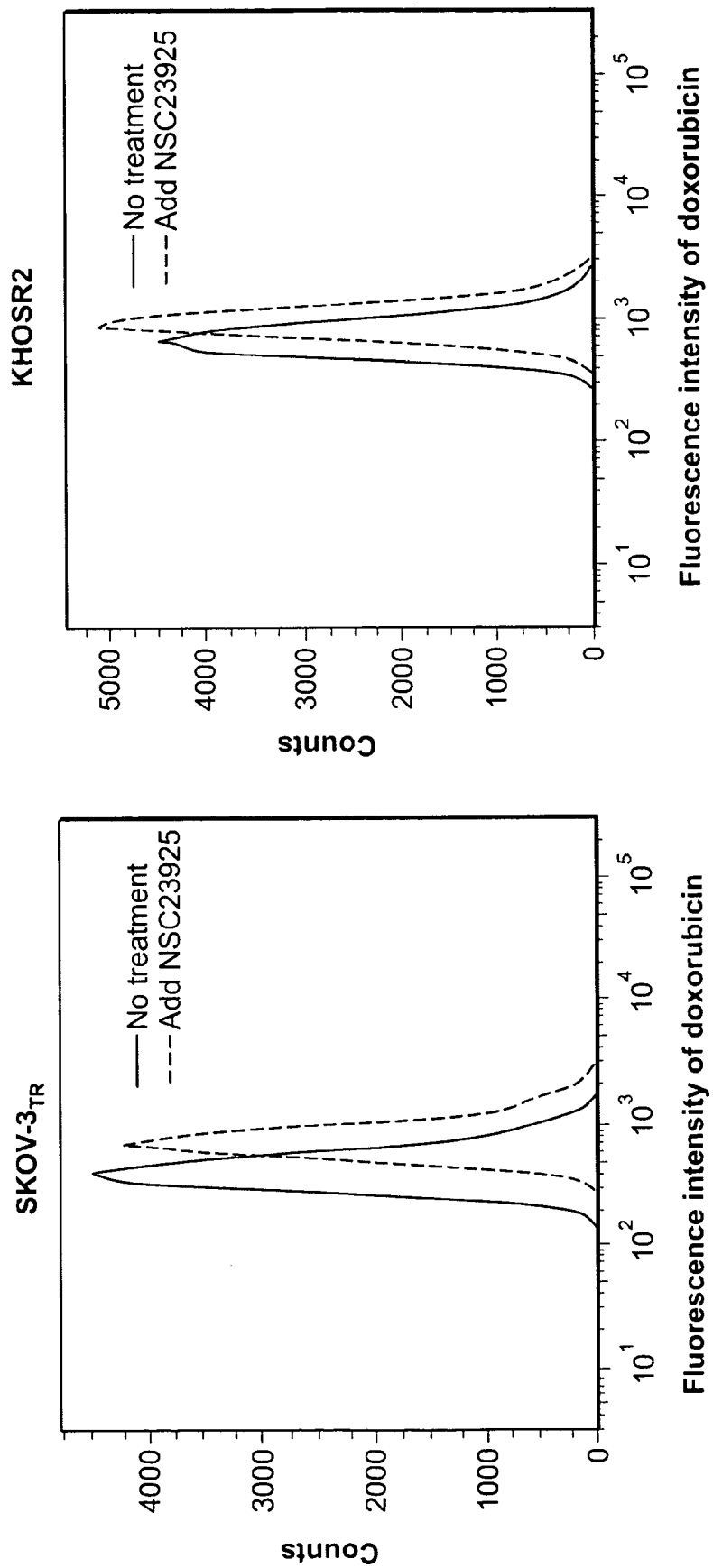
FIG. 9 depicts the intracellular retention of doxorubicin from multidrug resistant SKOV-3$_{TR}$ and KHOSR2 cells in the presence of 5 µM doxorubicin with or without treatment of NSC23925 (0.5 µM). Cells were treated for 1 hour before the flow cytometry analysis.

Reversal of MDR is usually manifested as an increased intracellular accumulation of chemotherapeutics, which can be achieved by disturbing Pgp1-mediated drug uptake and efflux. Therefore, the effect of NSC23925 on the uptake and efflux of several substrates of Pgp1 (calcein AM, for example) in SKOV-$3_{TR}$ and OVCAR$8_{TR}$ was examined. NSC23925 was shown to increase intracellular accumulation of calcein AM in these cell lines in a dose-dependent manner as determined by both image analysis (FIGS. 5A and 5C) and by microplate spectrofluorometer analysis (FIGS. 5B and 5D). NSC23925 has a prominent effect on the accumulation of calcein AM in these cells starting at a concentration as low as 1 nM. Half-maximal reversal of accumulation deficit was observed at 100 nM and near maximal at 500 nM. The potency of NSC23925 was significantly greater than that observed for verapamil and CsA (FIG. 5). In the control parental drug-sensitive cell lines SKOV-3 and OVCAR8, which do not overexpress Pgp1, NSC23925 had no evident effect on accumulation of calcein AM (FIGS. 5A and 5B). To confirm that NSC23925 inhibition of Pgp1-mediated efflux was not specific for only calcein AM, NSC23925 inhibition of efflux with other Pgp substrates including Rhodamine 123, mitoxantrone, dioc 2 and doxorubicin was evaluated. The fluorescence levels of these agents were monitored to determine cellular accumulation. It was observed that NSC23925 inhibited the efflux of these Pgp1 substrates from SKOV-3$_{TR}$ (FIG. 8). Flow cytometric analysis further confirmed that NSC23925 treatment increases the accumulation of doxorubicin in SKOV-3$_{TR}$ and KHOSR2 cells (FIG. 9).

Example 6

Pgp-ATPase Assay

Rational.

The increased accumulation of intracellular drug may be a result of decreased expression of Pgp or increased activity of Pgp. Pgp has an ATP-binding region. Pgp exhibits a highly drug-dependent ATP hydrolysis activity, and a variety of Pgp inhibitors, as well as Pgp substrates, can stimulate ATPase activity. The binding of ATP to the transporter's nucleotide-binding site is essential for substrate transport, and the hydrolysis of ATP by Pgp-ATPase is critical for restoring the transporter to its active conformational state. Thus, monitoring ATPase activity in cell membrane preparations, or purified membrane proteins, represents a method of identifying those compounds that interact with the drug efflux transporters.

Assay.

The Pgp-Glo™ Assay Systems (Promega) provide the necessary reagents for performing luminescent P-glycoprotein (Pgp)-ATPase assays. The ATPase assay provides a rapid, colorimetric, compound-independent measure of the concentration-dependence of any interaction of a drug with Ppg1. Untreated (NT), 100 µM Na$_3$VO$_4$, 100 µM Verapamil and 10 µM of a test compound-treated Pgp reactions were performed according to the manufacturer's protocol. Luminescence was read on a BMG LABTECH Polarstar Optima Luminometer. The decrease in luminescence of NT samples compared to samples plus Na$_3$VO$_4$ (ΔRLUbasal) represents basal Pgp-ATPase activity.

Pgp-ATPase assay is a valuable screening tool for determining if a drug interacts with Pgp. If a drug does not stimulate Pgp1-ATPase activity, the assay can still determine if the drug interacts with Pgp1 as an inhibitor of the ATPase activity stimulated by a known substrate, such as verapamil.

In this assay, a test compound is concluded to interact specifically with Pgp if it significantly modulates ATPase activities by >30%, at any one of the concentrations (0.05 to 50 µM) test.

Results.

Figure 6E:
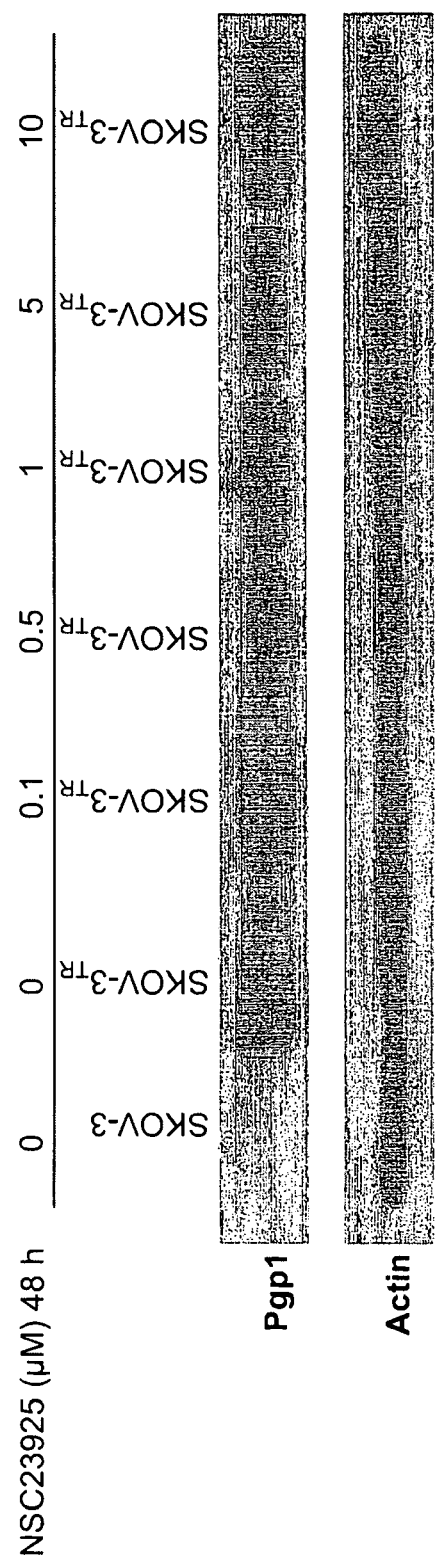
FIG. 6 depicts the effects of NSC23925 and verapamil on Pgp-ATPase activity. Untreated, 100 µM Na$_3$VO$_4$, 100 µM verapamil and 10 µM NSC23925-treated Pgp1 reactions were performed according to the manufacturer's protocol. Luminescence was read on a BMG LABTECH Polarstar Optima Luminometer. The decrease in luminescence of untreated samples compared to samples plus Na$_3$VO$_4$(ARLU$_{basal}$) represents basal Pgp1 ATPase activity. The decrease in luminescence of verapamil or NSC23925 treated samples represents Pgp1 ATPase activity. A: Decrease in luminescence of NSC23925 treated sample as compared with Na$_3$VO$_4$ or Verapamil treated sample. B: Replotted the stimulation of Pgp1 ATPase activity by verapamil and NSC23925. C and D: Dose dependence of verapamil (C) and NSC23925 (D) stimulation of Pgp1 ATPase activity. The data were representative of one of three independent experiments. *, P<0.001. E: Effect of NSC23925 on expression of Pgp1 in paclitaxel resistant cells. The paclitaxel resistant cell line SKOV-3$_{TR}$ was treated with different concentration of NSC23925 for 48 h. Equal amounts (20 µg protein) of total cell lysates were used for each sample. Pgp1 expression was determined by Western blot as described in the Examples section below.
Figure 7:
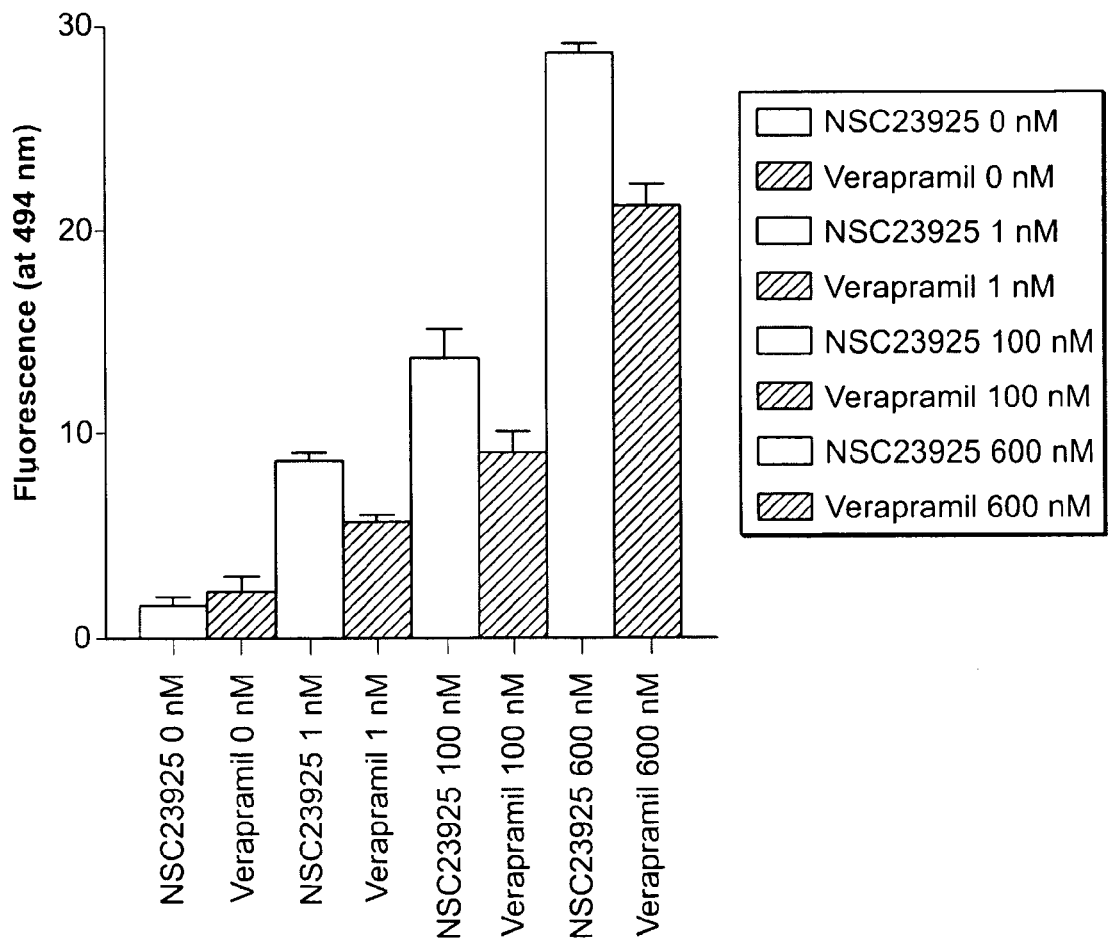
FIG. 7 depicts the effects of NSC23925 and verapamil on accumulation of calcein AM in SKOV-3$_{TR}$ cells.

The test results on NSC23925 are summarized in FIG. 6. NSC23925 significantly increased the ATPase activity in purified recombinant human Pgp1 membrane protein and this stimulation was dose-dependent (FIG. 6). However, the expression level of Pgp1 was not affected by different treatments with the addition of NSC23925 (up to 10 µM for 48 h) (FIG. E). These results suggest that NSC23925 stimulates Pgp1 ATPase activity by directly interacting with Pgp1. FIG. 6 demonstrates that NSC23925 and verapamil decrease in luminescence compared to the NT samples and samples plus Na$_3$VO$_4$ (ΔRLUbasal). FIG. 6 represents that verapamil and NSC23925 stimulated Pgp-ATPase activity. FIG. 6 demonstrates that NSC23925 stimulated the Pgp-ATPase activity, by >30%, and that this stimulation was dose-dependent.

Example 7

Fluorescence Microscopy

Assay.

For visualization of the effects of NSC23925 on the intracellular retention of calcein AM, doxorubicin, and mitoxantrone, 10,000 resistant cells were seeded on to Lab-Tek 8-well chamber slides on the day prior to the assay. Cells were then incubated with either, 0.25 µM calcein AM, 10 µM doxorubicin, or 10 µM mitoxantrone either alone or in the presence of NSC23925 in RPMI 1640 media for one hour at 37° C. Images were acquired by Nikon Eclipse Ti-U fluorescence microscope (Nikon Corp.) equipped with a SPOT RT digital camera (Diagnostic Instruments, Inc., Sterling Heights, Mich.).

Results.

Confocal fluorescence microscopy was used to verify that Pgp substrates were accumulating in the intracellular space of SKOV-3$_{TR}$ cells when co-administered with NSC23925. Cells were incubated with various fluorescent Pgp substrates including rhodamine 123, mitoxantrone, Dioc2, doxorobucin, and calcein AM in the presence and absence of NSC23925. Fluorescence emission was minimal in resistant cells in the absence of NSC23925 (top panel). However, upon incubation with 1 µM NSC23925, the cells became highly fluorescent (bottom panel). These findings demonstrate that NSC23925 is able to restore the accumulation of various Pgp substrates in cells expressing high levels of P-gp and that these substrates remain inside the cells. Similar results were found in other multidrug resistant cell lines (also highly express Pgp) such as OVCAR8$_{TR}$ and MCF-7$_{TR}$. These results were notable because these Pgp substrates are structurally distinct.

INCORPORATION BY REFERENCE

The contents of all references (including literature references, issued patents, published patent application, and co-pending patent applications) cited throughout this application are hereby expressly incorporated in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method of reducing drug resistance in a subject undergoing cancer treatment with administration of a chemotherapeutic drug, wherein the cancer is selected from the group consisting of: breast, respiratory tract, brain, reproductive organs, digestive tract, urinary tract, eye, liver, head and neck, thyroid, parathyroid, a distant metastasis of a solid tumor, lymphoma, sarcoma, and leukemia, said method comprising administering to a subject in need thereof an effective amount of (2-(4-Methoxyphenyl)quinolin-4-yl)(piperidin-2-yl)methanol or a pharmaceutically acceptable salt thereof, wherein (2-(4-methoxyphenyl)quinolin-4-yl)(piperidin-2-yl)methanol or a pharmaceutically acceptable salt thereof is administered at a dose that is lower than the dose required to produce cytotoxicity in said subject, thereby reducing drug resistance in said subject.

2. The method of claim 1, wherein (2-(4-methoxyphenyl)quinolin-4-yl)(piperidin-2-yl)methanol or a pharmaceutically acceptable salt thereof is administered to said subject at a dose at least 10 fold lower than that required to produce cytotoxicity in said subject.

3. The method of claim 2, wherein (2-(4-methoxyphenyl)quinolin-4-yl)(piperidin-2-yl)methanol or its pharmaceutically acceptable salt thereof is administered to said subject at a dose at least 50 fold lower than that required to produce cytotoxicity in said subject.

4. The method of claim 1, wherein (2-(4-methoxyphenyl)quinolin-4-yl)(piperidin-2-yl)methanol or a pharmaceutically acceptable salt thereof is administered to said subject at a dose between about 0.001 mg/Kg and about 100 mg/Kg.

5. The method of claim 1, wherein (2-(4-methoxyphenyl)quinolin-4-yl)(piperidin-2-yl)methanol or a pharmaceutically acceptable salt thereof is administered to said subject after the administration of said chemotherapeutic drug.

6. The method of claim 1, wherein said chemotherapeutic drug is selected from the group consisting of asparaginase, bleomycin, calcein-AM, carboplatin, carmustine, chlorambucil, cisplatin, colaspase, cyclophosphamide, cytarabine, dacarbazine, dactinomycin, daunorubicin, docetaxel, doxorubicin (adriamycine), epirubicin, etoposide, ET-743, 5-fluorouracil, gemcitabine, hexamethylmelamine, hydroxyurea, ifosfamide, irinotecan, leucovorin, lomustine, mechlorethamine, 6-mercaptopurine, mesna, methotrexate, mitomycin C, mitoxantrone, paclitaxel, prednisolone, prednisone, procarbazine, raloxifen, rhodamine-123, streptozocin, tamoxifen, thioguanine, topotecan, vinblastine, vincristine, vindesine, and zalypsis.

7. A method for treating cancer in a subject, wherein the cancer is selected from the group consisting of: breast, respiratory tract, brain, reproductive organs, digestive tract, urinary tract, eye, liver, head and neck, thyroid, parathyroid, a distant metastasis of a solid tumor, lymphoma, sarcoma, and leukemia, said method comprising a) identifying a subject undergoing cancer treatment with a chemotherapeutic drug and who has developed or is susceptible to developing drug resistance; and b) administering to said subject an effective amount of (2-(4-methoxyphenyl)quinolin-4-yl)(piperidin-2-yl)methanol or a pharmaceutically acceptable salt thereof, wherein said effective amount is sufficient to reduce drug resistance in said subject, thereby treating cancer in a subject.

8. The method of claim 7, wherein said method further comprises discontinuing said cancer treatment.

9. The method of claim 8, wherein said cancer treatment is discontinued prior to the administration of (2-(4-methoxyphenyl)quinolin-4-yl)(piperidin-2-yl)methanol or a pharmaceutically acceptable salt thereof.

10. The method of claim 8, wherein said cancer treatment is discontinued after the administration of (2-(4-methoxyphenyl)quinolin-4-yl)(piperidin-2-yl)methanol or a pharmaceutically acceptable salt thereof.

11. The method of claim 8, wherein said method further comprises administering to said subject a subsequent cancer treatment after the discontinuation of said cancer treatment and the administration of (2-(4-methoxyphenyl)quinolin-4-yl)(piperidin-2-yl)methanol or a pharmaceutically acceptable salt thereof.

12. The method of claim 11, wherein said subsequent cancer treatment is the same as said discontinued cancer treatment.

13. The method of claim 11, wherein said subsequent cancer treatment is different from said discontinued cancer treatment.

14. The method of claim 11, further comprising administering to said subject an additional effective amount of (2-(4-methoxyphenyl)quinolin-4-yl)(piperidin-2-yl)methanol or a pharmaceutically acceptable salt thereof after administration of said subsequent cancer treatment.

15. The method of claim 1, wherein the cancer is an ovarian cancer.

16. The method of claim 1, wherein the cancer is a breast cancer.

17. The method of claim 1, wherein the cancer is a leukemia.

18. The method of claim 1, wherein the cancer is a brain cancer.

19. The method of claim 1, wherein the cancer is a thyroid cancer.

20. The method of claim 7, wherein the cancer is an ovarian cancer.

21. The method of claim 7, wherein the cancer is a breast cancer.

22. The method of claim 7, wherein the cancer is a leukemia.

23. The method of claim 7, wherein the cancer is a brain cancer.

* * * * *

UNITED STATES PATENT AND TRADEMARK OFFICE
CERTIFICATE OF CORRECTION

PATENT NO. : 8,802,702 B2  
APPLICATION NO. : 13/144228  
DATED : August 12, 2014  
INVENTOR(S) : Duan et al.

Page 1 of 1

It is certified that error appears in the above-identified patent and that said Letters Patent is hereby corrected as shown below:

On the title page, column 2, Other Publications line 15, delete "gthe" and insert -- the --

In the Claims

Column 35, line 18, claim 6, delete "(adriamycine)," and insert -- (adriamycin) --

Column 35, line 23, claim 6, delete "raloxifen," and insert -- raloxifene, --

Signed and Sealed this  
Sixteenth Day of December, 2014

Michelle K. Lee  
*Deputy Director of the United States Patent and Trademark Office*